US007960532B2

(12) United States Patent
Light et al.

(10) Patent No.: US 7,960,532 B2
(45) Date of Patent: *Jun. 14, 2011

(54) POLYNUCLEOTIDES ENCODING ANTICOAGULANT ANTIBODIES

(75) Inventors: David Light, San Mateo, CA (US); Kirk McLean, Oakland, CA (US)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/503,893

(22) Filed: Jul. 16, 2009

(65) Prior Publication Data
US 2009/0317390 A1 Dec. 24, 2009

Related U.S. Application Data

(62) Division of application No. 10/512,215, filed as application No. PCT/US03/13521 on Apr. 30, 2003, now Pat. No. 7,579,000.

(60) Provisional application No. 60/376,566, filed on May 1, 2002.

(51) Int. Cl.
C07H 21/04 (2006.01)

(52) U.S. Cl. .................................. 536/23.53; 514/44 R

(58) Field of Classification Search ........................ None
See application file for complete search history.

(56) References Cited

U.S. PATENT DOCUMENTS

| | | | |
|---|---|---|---|
| 4,208,479 A | 6/1980 | Zuk | |
| 4,912,207 A | 3/1990 | Majerus | |
| 5,256,770 A | 10/1993 | Glaser | |
| 5,298,599 A | 3/1994 | Rezaie | |
| 5,466,668 A | 11/1995 | Glaser | |
| 5,506,134 A | 4/1996 | Soule | |
| 5,574,007 A | 11/1996 | Zushi | |
| 5,589,173 A | 12/1996 | O'Brien | |
| 5,827,824 A | 10/1998 | Light | |
| 5,843,442 A | 12/1998 | Soule | |
| 5,863,760 A | 1/1999 | Light | |
| 5,874,407 A | 2/1999 | Kelley | |
| 5,916,874 A | 6/1999 | Fujiwara | |
| 5,986,065 A | 11/1999 | Wong | |
| 6,063,763 A | 5/2000 | Light | |
| 6,274,142 B1 | 8/2001 | O'Brien | |
| 6,555,319 B2 | 4/2003 | Wong | |
| 6,632,791 B1 | 10/2003 | Light | |
| 7,250,168 B2 | 7/2007 | Light | |
| 2008/0019985 A1 | 1/2008 | Light | |
| 2008/0020965 A1 | 1/2008 | Light | |

FOREIGN PATENT DOCUMENTS

| | | |
|---|---|---|
| WO | WO 88/07543 | 10/1988 |
| WO | WO 88/09811 | 12/1988 |
| WO | WO 90/10081 | 9/1990 |
| WO | WO 98/40408 | 9/1998 |
| WO | WO 01/70984 | 9/2001 |
| WO | WO 01/98352 | 12/2001 |
| WO | WO 03/037911 | 5/2003 |

OTHER PUBLICATIONS

Adams et al., "Thrombin-cofactor Interactions: structural Insights into Regulatory Mechanisms," *Arteriosclerosis, Thrombosis, and Vascular Biology* 26, 1738-45, May 25, 2006.
Amit et al., 1986, *Science* 233, 747-53.
Bitonti et al., Pulmonary Delivery of an Erythropoietin Fc Fusion Protein in Non-human Primates Through an Immunoglobulin Transport Pathway, *Proc. Natl. Acad. Sci. USA* 101, 9763-68, Jun. 29, 2004.
Clarke et al., The Short Loop Between epidermal Growth Factor-like Domains 4 and 5 is Critical for Human Thrombomodulin Function, *J. Biol. Chem.* 268, 6309-15, Mar. 25, 1993.
Dahlback et al., "Blood Coagulation," *The Lancet* 355, 1627-32, May 6, 2000.
Dong et al., "P-selectin-targeting of the Fibrin Selective Thrombolytic Desmodus Rotundus Salivary Plasminogen Activator α1," *Thrombl Haemost.* 92, 956-65, 2004.
Esmon, "Regulation of Blood Coagulation," *Biochim. Biophys. Acta* 1477, 349-60, 2000.
Esmon, "The Roles of Protein C and Thrombomodulin in the Regulation of Blood Coagulation," *J. Biol. chem.* 264, 4743-4846, 1989.
Faelber et al., "The 1.85 Å Resolution Crystal Structures of Tissue factor in Complex with Humanized Fab D3h44 and of Free Humanized Fab D3h44: Revisiting the Solvation of antigen combining Sites," *J. Mol. Biol.* 313, 83-97, 2001.
Fuentes-Prior et al., "Structural Basis for the anticoagulant Activity of the Thrombin-thrombomodulin Complex," *Letters to Nature* 404, 518-25, Mar. 30, 2000.
Gresele et al., "Novel Approaches to the Treatment of Thrombosis," *Tresnds Pharmacol. Sci.* 23, 25-32, 2002.
Haber et al., "Antibody Targeting as a Thrombolytic strategy," *Ann. NY Acad. Sci.* 667, 365-81, 1992.
Hall et al., "Thrombin Interacts with Thrombomodulin, Protein C, and Thrombin-activatable Fibrinolysis Inhibitor via Specific and Distinct Domains," *J. Biol. Chem.* 274, 22510-16, Sep. 3, 1999.
Janeway et al., *Immunobiology*, 3rd ed., Garland Publishin Inc., 1997, pp. 3:7-3:9.
Moons et al., "Tissue Factor and Coronary Artery Disease," *Cardiovascular Res.* 53, 313-25, 2002.

(Continued)

Primary Examiner — Michael Szperka
(74) *Attorney, Agent, or Firm* — Banner & Witcoff, Ltd.

(57) ABSTRACT

This invention relates to novel antibodies that bind with greater affinity to the factor VIIa/tissue factor (FVIIa/TF) complex than to tissue factor (TF) alone, do not compete for binding to TF with FVII and FX, an inhibit FX activation. The antibodies bind at the site of injury and prevent the initiation of thrombosis. The antibodies can be used to treat a variety of thrombotic conditions including but not limited to deep vein thrombosis, disseminated intravascular coagulation, and acute coronary syndrome.

5 Claims, 8 Drawing Sheets

OTHER PUBLICATIONS

Nagashima et al., "Alanine-scanning Mutagenesis of the epidermal Growth Factor-like Domains of Human Thrombomodulin Identifies Critical Residues for its Cofactor Activity," *J. Biol. Chem. 268*, 2888-92, Feb. 5, 1993.

On-line Medical dictionary definition of synergy, downloaded Oct. 26, 2006 from cancerweb.ncl.ac.uk, 1 page.

Rudikoff et al., *Proc. Natl. Acad. Sci. USA 79*, 1979-83, 1982.

Skolnick et al., *Trends in Biotechnology 18*, 34-39, 2000.

Stedman's Medical dictionary, 27th ed., 2000, definition of synergism, downloaded Oct. 26, 2006 from thomsonhc.com, 2 pages.

Wang et al., "Elements of the Primary Structure of thrombomodulin Required for Efficient Thrombin-activable Fibrinolysis Inhibitor Activation," *J. Biol. Chem. 275*, 22942-47, Jul. 28, 2000.

Whisstock et al., *Quarterly Review of Biophysics 36*, 307-40, 2003.

Heyman et al., *J. Immunol. 134*, 4018-23, 1985.

Chapman et al., *Nature Biotechnol. 17*, 780-83, 1999.

Harlow et al., *Antibodies, A Laboratory Manual*, Cold Spring Harbor Laboratory, pp. 340-341, 1988.

POLYNUCLEOTIDES ENCODING ANTICOAGULANT ANTIBODIES

This application is a division of Ser. No. 10/512,215 filed on Jan. 12, 2005, which is a national stage application of PCT/US03/13521 filed on Apr. 30, 2003, which claims priority to Ser. No. 60/376,566 filed on May 1, 2002. Each of these applications is incorporated by reference herein in its entirety.

This application incorporates by reference the contents of a 7.57 kb text file created on Aug. 27, 2009 and named "SN12503893_sequence_listing.txt," which is the sequence listing for this application.

BACKGROUND

Maintaining the proper balance between procoagulant and anticoagulant activity within blood vessels is essential for normal hemostasis (Davie, E. W. et al. (1991) *Biochemistry*, 30(43):10363-10370). Perturbing the balance toward coagulation leads to thrombosis, which can cause heart attack, stroke, pulmonary embolism, and venous thrombosis. There is a need for more effective and safer anticoagulants for the treatment of specific thrombotic disorders.

Tissue factor ("TF") is a transmembrane glycoprotein that is the major initiator of the coagulation cascade (Nemerson, Y. (1995) *Thromb. Haemost.* 74(1):180-184). Under normal physiological conditions active TF is not in contact with blood. During vascular injury, exposure to blood of subendothelial TF and collagen leads to activation of coagulation factors and platelets and subsequently to hemostatic plug formation. Exposed TF acts as a cofactor for the factor VIIa ("FVIIa") catalyzed activation of factor IX ("FIX") and factor X ("FX"), critical components of the intrinsic tenase and prothrombinase complexes, respectively. This leads to rapid formation of FXa and thrombin. Thrombin then cleaves fibrinogen to fibrin, which subsequently polymerizes to form the fibrin clot. The inappropriate induction of TF expression in a variety of clinical settings can lead to life threatening thrombosis and/or contribute to pathological complications. TF exposure following plaque rupture is believed to be responsible for thrombotic occlusion leading to acute myocardial infarction and stroke. In these settings, proinflammatory signaling pathways activated by coagulation factors also contribute to edema formation and increased infarct size. Vascular injury associated with angioplasty leads to upregulation of TF on SMC's which is believed to induce cell signaling pathways associated with restenosis. TF overexpression in cancer and gram-negative sepsis leads to life threatening thrombosis and activation of inflammatory pathways.

The FVIIa/TF complex is involved in the pathogenic mechanism in a variety of thrombotic diseases and the circulating level of TF is a risk factor for certain patients. FVIIa and TF play unique roles in vascular injury in maintaining hemostasis and initiating thrombosis. TF is expressed in the adventitia normally, but is upregulated and expressed inappropriately in the media and neointima in vascular disease. TF expression in atherosclerotic plaques is increased and shielded from the blood by a thin fibrous cap that may rupture to expose TF. Surgical interventions such as balloon angioplasty, stenting, or endarterectomy damage the vessel wall and expose underlying TF. In the atherosclerotic, lipid-rich, thin-walled plaque, spontaneous rupture or endothelial erosion leads to TF exposure and thrombosis, resulting in unstable angina and myocardial infarction. TF can circulate in cell-derived microparticles and circulating TF levels are elevated in unstable angina, suggesting that this circulating TF may contribute to thrombus formation (Soejima, H. et al. (1999) *Circulation* 99(22):2908-2913). Often cancer is associated with a hypercoagulable state attributed to overexpression of TF on tumor cells. This predisposes the patient to deep vein thrombosis, pulmonary embolism and low grade disseminated intravascular coagulation ("DIC"). DIC results in microvascular fibrin deposition contributing to multi-organ failure.

Protein based anticoagulants that target TF include TF neutralizing antibodies, active site inhibited factor VIIa ("FVIIai"), tissue factor pathway inhibitor ("TFPI"), and Nematode anticoagulant protein ("NAPC2"). Results from acute arterial injury models of thrombosis indicate that protein based inhibitors of FVIIa/TF are effective antithrombotics, with less bleeding compared to heparin, direct thrombin inhibitors, platelet inhibitors, and FXa inhibitors (Himber, J. et al. (2001) *Thromb. Haemost.* 85:475-481; Harker, L. A. et al. (1995) *Thromb. Haemost.* 74(1):464-472. In addition, FVIIa/TF inhibition is superior to other anticoagulants (e.g., heparin, FXa inhibitors) in preventing neointimal thickening and vascular stenosis following balloon injury (Jang, Y. et al. (1995) *Circulation* 92(10):3041-3050).

Inhibition of TF, FVIIa or the FVIIa/TF complex is an efficacious antithrombotic approach for preventing DIC and reducing mortality in experimental models of sepsis. TFPI analogs prevent both thromboplastin and endotoxin-induced DIC in rabbits (Day, K. C. et al. (1990) *Blood* 76:1538-1545; Bregengard, C. et al. (1993) *Blood Coagul. Fibrinolysis* 4:699-706). Monoclonal antibodies against FVIIa (Biemond, B. J. et al. (1995) *Thromb. Haemost.* 73:223-230) or (Levi, M. et al. (1994) *J. Clin. Invest.* 93:114-120) prevent endotoxin-induced DIC in monkeys. TF neutralizing antibodies, FVIIai, and TFPI, inhibit DIC and reduce mortality in a baboon model of *E. coli*-induced sepsis (Creasey, A. A. et al. (1993) *J. Clin. Invest* 91:2850-2860; Taylor, F. B. et al. (1991a) *Blood* 78:364-368; Taylor, F. B. et al. (1991b) *Circ. Shock* 33:127-134; Taylor, F. B. (1996) *Haemostasis Suppl.* 1 26:83-91). Both free FXa and the FVIIa/TF/FXa complex are known to induce the production of proinflammatory cytokines that are associated with an increased risk of death in patients with sepsis (Riewald, M. et al. (2001) *Proc. Natl. Acad. Sci. USA* 98:7742-7747). Interestingly, FVIIai was shown to lower plasma levels of IL-6 and IL-8 in the baboon model (Taylor, F. B. et al. (1998) *Blood* 91:1609-1615), suggesting that FVIIa/TF inhibition may have additional antiinflammatory effects not shared by other anticoagulant mechanisms.

Several antibodies that are effective anticoagulants, which bind to and neutralize either TF or the FVIIa/TF complex or both, have been described (see e.g., Carson, S. D. et al. (1985) *Blood* 66(1):152-156; Tanaka, H. et al. (1985) *Thromb. Res.* 40(6):745-756; Kirchhofer, D. et al. (2000) *Throomb. Haemost.* 84(6); 1072-1081; Kirchhofer, D. et al. (2001) *Biochemistry* 40(3):675-682; Faelber, K. et al., (2001) *J. Mol. Biol.* 313:83-97; and U.S. Pat. Nos. 5,506,134, 5,986,065, and 6,274,142). The TF targeted antibodies of the present invention are effective anticoagulants that have improved characteristics over previously described TF antibodies. In particular, the antibodies of the invention bind with greater affinity to the FVIIa/TF complex than to TF alone, and are non-competitive with FVII or FX for binding to TF.

SUMMARY OF THE INVENTION

The present invention provides antibodies, which act as anticoagulants, that bind with greater affinity to the factor VIIa/tissue factor ("FVIIa/TF") complex than to tissue factor ("TF") alone. In one embodiment, the antibodies of the invention bind with at least 2-fold greater affinity to the FVIIa/TF complex than to TF alone, as measured in a microcalorimetry assay. In a preferred embodiment, the antibodies of the invention bind with at least 5-fold greater affinity to the FVIIa/TF complex than to TF alone. In a more preferred embodiment, the antibodies of the invention bind with at least 10-fold greater affinity to the FVIIa/TF complex than to TF alone. In another embodiment, the antibodies of the invention do not compete for binding to TF with one or more coagulation factors selected from the group consisting of factors VII ("FVII"), IX ("FIX"), and X ("FX"). In a preferred embodiment, the antibodies of the invention do not compete for binding to TF with FVII and with FX. In a more preferred embodiment, the antibodies of the invention bind with greater affinity to the FVIIa/TF complex than to TF alone and do not compete for binding to TF with FVII and with FX.

The anticoagulant antibody of this invention targets and binds to the FVIIa/TF complex at the site of injury and inhibits factor X ("FX") activation, thus preventing thrombus formation, and thereby performing effectively as an anticoagulant in the treatment of certain diseases including, but not limited to, sepsis, disseminated intravascular coagulation, ischaemic stroke, deep vein thrombosis, acute coronary syndromes, thrombotic complications following angioplasty, and coagulopathy in advanced cancer. Further, the antibody has use in microvascular surgery, skin and vein grafts, and organ transplants.

In another aspect, the invention provides pharmaceutical compositions comprising the subject antibodies.

In another aspect, the invention provides for a method of protecting a patient against thrombus formation comprising administering a therapeutically effective amount of the antibody of this invention to said patient, and thereby inhibiting the generation of thrombin without directly affecting other coagulation parameters, such as the activation and aggregation of platelets.

In another aspect, the invention relates to a method for reducing and treating deep vein thrombosis ("DVT") or disseminated intravascular coagulation ("DIC") or acute coronary syndrome or cancer with evidence of coagulopathy in a patient comprising administering a therapeutically effective amount of the antibody of the invention to said patient.

In another aspect, the invention relates to a method for regulating the inflammatory response in a patient comprising administering a therapeutically effective amount of the antibody of the invention to said patient.

In yet another aspect, the antibody of the invention can be used to form a non-thrombogenic coating on the surface of medical devices contacting blood.

In still another aspect, the invention relates to a kit comprising an antibody of the invention that binds to the FVIIa/TF complex. Alternately, the kit may comprise DNA sequences encoding the antibody components.

Also disclosed are methods of making the antibodies of the invention, both recombinant and synthetic.

DETAILED DESCRIPTION OF THE INVENTION

Figure 1:
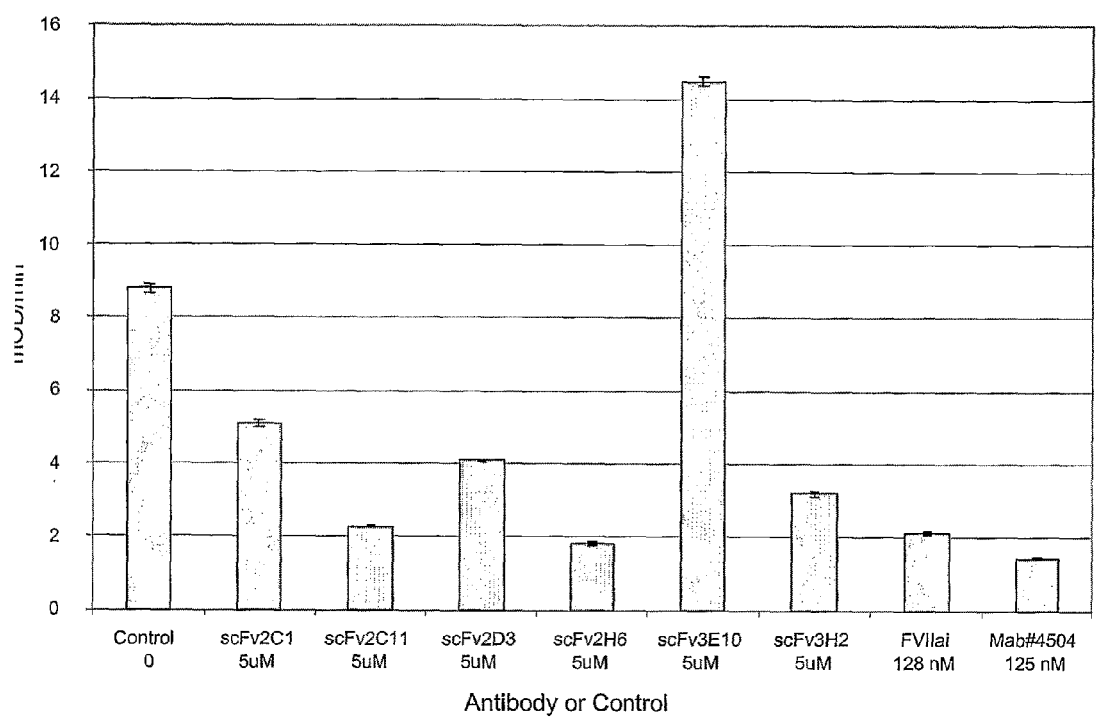
FIG. 1. Activity of TF-binding single chain antibodies in the sTF/FVIIa peptide hydrolysis assay. The sTF/FVIIa peptide hydrolysis assay was performed as described under Example 4 using an equilibrium mixture of FVIIa (5 nM) and sTF (10 nM), based on the affinity of FVIIa for sTF ($K_{D(app)}$=~10 nM). Hydrolysis of the chromogenic peptide substrate S2266 was monitored as described. Final concentrations of the bacterially expressed single chain antibodies, and the control proteins FVIIai (FVIIa inactivated by a chloromethylketone peptide, PPACK) and Mab#4504 (American Diagnostica), are indicated.

The anticoagulant antibody of the present invention is an antibody that binds with greater affinity to the factor VIIa/tissue factor ("FVIIa/TF") complex than to tissue factor ("TF") alone. The antibody of the invention binds with at least 2-fold greater affinity, preferably at least 5-fold greater affinity, and more preferably at least 10-fold greater affinity, to the FVIIa/TF complex than to TF alone. The antibody of the invention also does not compete for binding to TF with one or more coagulation factors selected from the group consisting of factor VII ("FVII"), factor IX ("FIX"), and factor X ("FX"). Preferably, the antibody of the invention does not compete for binding to TF with FVII and with FX.

DEFINITIONS

In describing the present invention, the following terms are defined as indicated below.

"Recombinant proteins or polypeptides" refer to proteins or polypeptides produced by recombinant DNA techniques, i.e., produced from cells, microbial or mammalian, transformed by an exogenous DNA construct encoding the desired polypeptide. Proteins or polypeptides expressed in most bacterial cultures will be free of glycan. Proteins or polypeptides expressed in yeast may have a glycosylation pattern different from that expressed in mammalian cells.

"Native" proteins or polypeptides refer to proteins or polypeptides recovered from a source occurring in nature. The term "native antibody" would include naturally occurring antibodies and fragments thereof.

A DNA "coding sequence" is a DNA sequence which is transcribed into mRNA and translated into a polypeptide in a host cell when placed under the control of appropriate regulatory sequences. The boundaries of the coding sequence are determined by a start codon at the 5' N-terminus and a translation stop codon at the 3' C-terminus. A coding sequence can include prokaryotic sequences, cDNA from eukaryotic mRNA, genomic DNA sequences from eukaryotic DNA, and synthetic DNA sequences. A transcription termination sequence will usually be located 3' to the coding sequence.

"Nucleotide sequence" is a heteropolymer of deoxyribonucleotides (bases adenine, guanine, thymine, or cytosine). DNA sequences encoding the antibodies of this invention can be assembled from synthetic cDNA-derived DNA fragments and short oligonucleotide linkers to provide a synthetic gene that is capable of being expressed in a recombinant expression vector. In discussing the structure of particular double-stranded DNA molecules, sequences may be described herein according to the normal convention of giving only the sequence in the 5' to 3' direction along the nontranscribed strand of cDNA.

"Recombinant expression vector" is a replicable DNA construct used either to amplify or to express DNA encoding the antibodies of the present invention. An expression vector contains DNA control sequences and a coding sequence. DNA control sequences include promoter sequences, ribosome binding sites, polyadenylation signals, transcription termination sequences, upstream regulatory domains and enhancers. Recombinant expression systems as defined herein will express the antibodies upon induction of the regulatory elements.

"Transformed host cells" refer to cells that have been transformed and transfected with exogenous DNA. Exogenous DNA may or may not be integrated (covalently linked) to chromosomal DNA making up the genome of the cell. In prokaryotes and yeast, for example, the exogenous DNA may be maintained on an episomal element, such as a plasmid or stably integrated into chromosomal DNA. With respect to eukaryotic cells, a stably transformed cell is one in which the exogenous DNA has become integrated into the chromosome replication. This stability is demonstrated by the ability of the eukaryotic cell lines or clones to produce a population of daughter cells containing the exogenous DNA The terms "analog", "fragment", "derivative", and "variant", when referring to the antibodies of this invention means analogs, fragments, derivatives, and variants of the antibodies which retain substantially the same biological function or activity, as described further below.

An "analog" includes a pro-polypeptide which includes within it, the amino acid sequence of the antibody of this invention. The active antibody of this invention can be cleaved from the additional amino acids that complete the pro-antibody molecule by natural, in vivo processes or by procedures well known in the art such as by enzymatic or chemical cleavage. For example, the recombinant scFV(TF)3e10 polypeptide (SEQ ID NO:1) is expressed as a 282 amino acid pro-polypeptide which is then processed in vivo to release the 264 amino acid active mature polypeptide.

A "fragment" is a portion of the antibody of the invention that retains substantially similar functional activity, as shown in the in vitro assays disclosed herein as described further below.

A "derivative" includes all modifications to the antibodies of this Invention that substantially preserve the functions disclosed herein and include additional structure and attendant function, e.g., PEGylated antibodies which have greater half-life, and biotinylated antibodies, as described further below. A derivative also includes N- or O-linked glycosylated antibodies that can be generated by inserting N- or O-glycosylation sites into the antibody sequences by standard recombinant DNA technology.

"Substantially similar functional activity" and "substantially the same biological function or activity" each means that the degree of biological activity that is within about 30% to 100% or more of that biological activity demonstrated by the polypeptide to which it is being compared when the biological activity of each polypeptide is determined by the same procedure or assay. For example, an antibody that has substantially similar functional activity to the antibody of Example 1 (SEQ ID NO:1) is one that, when tested in the sTF/FVIIa peptide hydrolysis and FX activation assays described in Example 4, demonstrates the ability to bind to and neutralize the FVIIa/TF complex.

"Similarity" between two polypeptides is determined by comparing the amino acid sequence and its conserved amino acid substitutes of one polypeptide to the sequence of a second polypeptide. Such conservative substitutions include those described above in *The Atlas of Protein Sequence and Structure* 5 by Dayhoff (1978) and by Argos (1989) *EMBO J.* 8:779-785. For example, amino acids belonging to one of the following groups represent conservative changes:

```
Ala, Pro, Gly, Gln, Asn, Ser, Thr:

Cys, Ser, Tyr, Thr;

Val, Ile, Leu, Met, Ala, Phe;
```

-continued

Lys, Arg, His;

Phe, Tyr, Trp, His; and

Asp, Glu.

"Antibody" as used herein includes intact immunoglobulin ("Ig") molecules, as well as fragments thereof, such as Fab, F(ab')$_2$, and Fv, which are capable of binding an epitope of the selected target protein, for example, soluble TF ("sTF"). Typically, at least 6, 8, 10, or 12 contiguous amino acids are required to form an epitope. However, epitopes which involve non-contiguous amino acids may required more, e.g. at least 15, 25, or 50 amino acids.

All other technical terms used herein have the same meaning as is commonly used by those skilled in the art to which the present invention belongs.

Antibodies of the Invention and their Generation:

The anticoagulant antibodies of this invention bind with greater affinity to the factor VIIa/tissue factor ("FVIIa/TF") complex than to tissue factor ("TF") alone. In a preferred embodiment, the antibodies of the invention bind with at least 2-fold greater affinity to the FVIIa/TF complex than to TF alone, more preferably with at least 5-fold greater affinity, and still more preferably with at least 10-fold greater affinity, as measured in a microcalorimetry assay. In another preferred embodiment of this invention, the antibodies also do not compete with one or more coagulation factors selected from the group consisting of factors VII ("FVII"), IX ("FIX"), and X ("FX") for binding to TF. In a more preferred embodiment, the antibodies of the invention do not compete with FVII and with FX for binding to TF. In the most preferred embodiment, the antibodies of the invention bind with greater affinity to the FVIIa/TF complex than to TF alone and do not compete for binding to TF with FVII and with FX.

Generally speaking, an antibody that binds specifically to a selected target protein (e.g., the FVIIa/TF complex or TF) provides a detection signal at least 5-, 10-, or 20-fold higher than a detection signal provided with other proteins when used in an immunochemical assay. Preferably, antibodies that bind specifically to the selected target protein do not detect other proteins in immunochemical assays and can immunoprecipitate the target protein from solution.

The selected target protein can be used to immunize a mammal, such as a mouse, rat, rabbit, guinea pig, monkey, or human to produce polyclonal antibodies. If desired, the target protein can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g., lysolecithin, pluronic polyols, polyanions, peptides, oil emulsions, keyhole limpet hemocyanin, and dinitrophenol). Among adjuvants used in humans, BCG (bacilli Calmette-Guerin) and *Cornybacterium parvum* are especially useful.

Monoclonal antibodies that bind specifically to a selected target protein can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al. (1985) *Nature* 256:495-497; Kozbor et al. (1985) *J. Immunol. Methods* 81:31-42; Cote et al. (1983) *Proc. Natl. Acad. Sci. USA* 80:2026-2030; and Cote et al. (1984) *Mol. Cell Biol.* 62:109-120).

In addition, techniques developed for the production of "chimeric antibodies," the splicing of mouse antibody genes to human antibody genes to obtain a molecule with appropriate antigen specificity and biological activity, can be used (Morrison et al. (1984) *Proc. Natl. Acad. Sci. USA* 81:6851-6855; Neuberger et al. (1984) *Nature* 312:604-608; Takeda et al. (1985) *Nature* 314:452-454). Monoclonal and other antibodies also can be "humanized" to prevent a patient from mounting an immune response against the antibody when it is used therapeutically. Such antibodies may be sufficiently similar in sequence to human antibodies to be used directly or may require alteration of a few key residues. Sequence differences between rodent antibodies and human sequences can be minimized by replacing residues which differ from those in the human sequences by site directed mutagenesis of individual residues or by grafting of entire complementarity determining regions. Alternatively, humanized antibodies can be produced using recombinant methods, as described in GB2188638B. Antibodies that bind specifically to a selected target protein can contain antigen-binding sites which are either partially or fully humanized, as disclosed in U.S. Pat. No. 5,565,332.

Alternatively, techniques described for the production of single chain antibodies can be adapted using methods known in the art to produce single chain antibodies ("scFv") that bind specifically to a selected target protein. Antibodies with related specificity, but of distinct idiotypic composition, can be generated by chain shuffling from random combinatorial Ig libraries (Burton (1991) *Proc. Natl. Acad. Sci. USA* 88:11120-11123).

Single chain antibodies also can be constructed using a DNA amplification method, such as PCR, using hybridoma cDNA as a template (Thirion et al. (1996) *Eur. J. Cancer Prev.* 5:507-511). Single chain antibodies can be mono- or bispecific, and can be bivalent or tetravalent. Construction of tetravalent, bispecific single chain antibodies is taught, for example, In Coloma and Morrison (1997) *Natl. Biotechnol.* 15:159-163. Construction of bivalent, bispecific single chain antibodies is taught in Mallendar and Voss (1994) *J. Biol. Chem.* 269:199-216.

A nucleotide sequence encoding a single chain antibody can be constructed using manual or automated nucleotide synthesis, cloned into an expression construct using standard recombinant DNA methods, and introduced into a cell to express the coding sequence. Alternatively, single chain antibodies can be produced directly using, for example, filamentous phage display technology (Verhaar et al. (1995) *Int. J. Cancer* 61:497-501; and Nicholls et al. (1993) *J. Immunol. Meth.* 165:81-91).

Antibodies that bind specifically to a selected target protein can also be produced by inducing in vivo production in the lymphocyte population or by screening Ig libraries or panels of highly specific binding reagents as disclosed in the literature (Orlandi et al. (1989) *Proc. Natl. Acad. Sci. USA* 86:3833-3837; Winter et al. (1991) *Nature* 349:293-299).

The DNA encoding the antibody of the invention may be cloned in cDNA or in genomic form by any cloning procedure known to those skilled in the art. See for example, Sambrook, J. F. at al. (1989) *Molecular Cloning: A Laboratory Manual*, Cold Spring Harbor Laboratory (1989), which is herein incorporated by reference).

In the case where the antibody is a monoclonal antibody, once a DNA sequence has been identified that encodes a Fv region which when expressed shows specific binding activity, antibodies comprising that Fv region may be prepared by methods known to one of skill In the art. Thus, for example, Chaudhary, V. K. et al. (1989) *Nature* 339(6223): 394-397; Batra, J. K. et al. (1990) *J. Biol. Chem.* 265(25):15198-15202; Batra, J. K. et al. (1989) *Proc. Natl. Acad. Sci. USA* 86(21): 8545-8549; Chaudhary, V. K. et al., (1990) *Proc. Natl. Acad. Sci. USA* 87(3):1066-1070, all incorporated by reference, describe the preparation of various single chain antibody proteins.

In a preferred approach, the TF-binding antibodies of the invention are single chain antibodies, which are prepared using a phage display library. The epitope-binding region of a single chain antibody is made up from two variable region domains: one from the heavy chain and the other from the light chain. In the first step of constructing a phage display library, the variable genes ($V_H$ (from IgM) $V_\kappa$ and $V_L$) are PCR cloned from pooled mRNA from human bone marrow, lymph node and spleen using a set of family specific primers. The resultant pCITE-$V_H$ ($3.8 \times 10^9$ members), pZ604-$V_\kappa$ ($1.6 \times 10^7$) and pZ604-$V_L$ ($3.2 \times 10^7$) libraries represent a permanent and high diversity of V genes. The $V_H$ genes are then amplified from pCITE-$V_H$ library. The $V_\kappa$ and $V_L$ genes are PCR amplified from the pZ604-$V_\kappa$ and pZ604-$V_L$ library with reverse $J_H$ and linker sequence at the 5' end. The gel purified $V_H$, $V_\kappa$, and $V_L$ containing PCR products are then spliced together to make the scFv gene repertoire. The scFv gene repertoire is cloned to a phagemid vector pZ603, and the ligation product is electroporated into competent TG1 *E. Coli* cells to generate the scFv phage display library, HuPhabL3, with $5.2 \times 10^9$ individual transformants (Kay, B. K. et al. (1996) *Phage Display of Peptides and Proteins: A Laboratory Manual*, Academic Press, San Diego Calif.; Marks, J. D. et al. (1991) *J. Mol. Biol.* 222(3):581-597; Sheets, M. D. et al. (1998) *Proc. Natl. Acad. Sci. USA* 95(11):6157-6162).

The TF-binding phage from the scFv phage display library are selected, amplified, and subsequently identified using panning techniques that are well known in the art. Soluble TF is immobilized in plastic tubes, and non-fat milk can be used to reduce non-specific binding to the plastic. The population of scFv phage is exposed to the immobilized sTF in the plastic tubes, and the unbound phage are removed by extensive washing. The TF-binding scFv phage are eluted from the tubes and then amplified by infecting TG1 *E. coli* cells in solution. This panning procedure is repeated three times, and the resulting TF-binding scFv phage are isolated by transforming TG1 cells. Transformants expressing TF-binding antibodies are identified using a standard ELISA with sTF immobilized onto plastic in 96-well dishes. The DNA of the single chain antibody inserts of ELISA-positive transformants are sequenced. Based on DNA sequencing, six unique single chain antibodies, scFv(TF)2c1, scFv(TF)2c11, scFv (TF)2d3, scFv(TF)2h6, scFv(TF)3e10 and scFv(TF)3h2, are identified herein, and were expressed and purified from *E. coli*, and characterized as described below under Example 5. Expression and Purification of Antibodies of the Invention:

There are several ways to express the recombinant antibodies of the invention in vitro, including *E. coli*, baculovirus, yeast mammalian cells or other expression systems. Methods for the expression of cloned genes in bacteria are well known. To obtain high level expression of a cloned gene in a prokaryotic system, it is essential to construct expression vectors that contain, at the minimum, a strong promoter to direct mRNA transcription termination. Examples of regulatory regions suitable for this purpose are the promoter and operator region of the *E. coli* beta-glucosidase gene, the *E. coli* tryptophan biosynthetic pathway, or the leftward promoter from phage Lambda. The inclusion of selection markers in DNA vectors transformed in *E. coli* is useful. Examples of such markers include the genes specifying resistance to ampicillin, tetracycline, or chloramphenicol.

Of the higher eukaryotic cell systems useful for expression of the antibodies of the invention, and analogs, fragments, derivatives or variants thereof, there are numerous cell systems to select from. Illustrative examples of mammalian cell lines include but are not limited to RPMI 7932, VERO and HeLa cells, Chinese hamster ovary (CHO) cell lines, WI38, BHK, COS-7, C127 or MDCK cell lines. A preferred mammalian cell lines is CHL-1. When CHL-1 is used hygromycin is included as a eukaryotic selection marker. CHL-1 cells are derived from RPMI 7032 melanoma cells, a readily available human cell line. The CHL-1 cell line has been deposited with ATCC according to conditions of the Budapest Treaty and has been assigned #CRL 9446, deposited Jun. 18, 1987. Cells suitable for use in this invention car commercially available from the ATCC. Illustrative cell lines include *Spodoptera frugiperda* and *Bombyx mori*.

The prokaryotic system, *E. coli*, is not able to do post-translational modification, such as glycosylation. In addition, proteins with complex disulfide patterns are often misfolded when expressed in *E. coli*. With the prokaryotic system, the expressed protein is either present in the cell cytoplasm in an insoluble form so-called inclusion bodies, found in the soluble fraction after the cell has lysed, or is directed into the periplasm by addition of appropriate secretion signal sequences. If the expressed protein is in insoluble inclusion bodies, solubilization and subsequent refolding of the inclusion bodies is usually required.

Many prokaryotic expression vectors are known to those of skill in the art such as pKK223-3 (Pharmacia Fine Chemicals, Uppsala, Sweden), pKK233-2 (Clontech, Palo Alto, Calif., USA), and pGEM1 (Promega Biotech, Madison, Wis., USA), which are commercially available.

Promoters commonly used in recombinant microbial expression systems include the beta-lactamase (penicillinase) and lactose promoter system (Chang, A. C. et al. (1978) *Nature* 275(5681):617-624; Goeddel, D. V. et al. (1979) *Nature* 281(5732):544-548), the tryptophan (trp) promoter system (Goeddel, D. V. et al. (1980) *Nucl. Acids Res.* 8(18): 4057-4074) and tac promoter (Maniatis, T. et al., Molecular Cloning: A Laboratory Manual, Cold Spring Harbor Laboratory (1982)). Another useful bacterial expression system employs the lambda phage pL promoter and clts857 thermoinducible repressor (Bernard, H. U. et al. (1979) *Gene* 5(1):59-76; Love, C. A. et al. (1996) *Gene* 176(1-2):49-53). Recombinant antibodies may also be expressed in yeast hosts such as *Saccharomyces cerevisiae*. It usually gives the ability to do various post-translational modifications. The expressed antibody can be secreted into the culture supernatant where not many other proteins reside, making purification easier. Yeast vectors for expression of the antibodies in this invention contain certain requisite features. The elements of the vector are generally derived from yeast and bacteria to permit propagation of the plasmid in both. The bacterial elements include an origin of replication and a selectable marker. The yeast elements include an origin of replication sequence (ARS), a selectable marker, a promoter, and a transcriptional terminator.

Suitable promoters in yeast vectors for expression include the promoters of TRP1 gene, the ADH1 or ADHII gene, acid phosphatase (PH03 or PH05) gene, isocytochrome gene, or the promoters involved with the glycolytic pathway, such as the promoter of enolase, glyceraldehyde-3-phosphate dehydrogenase (GADPH), 3-phosphoglycerate kinase (PGK), hexokinase, pyruvate kinase, triosephosphate isomerase and phosphoglucose isomerase (Hitzeman, R. A. et al. (1980) *J. Biol. Chem.* 255(24):12073-12080; Hess, B. et al., (1968) *J. Adv. Enzyme Reg.* 7:149-167; and Holland, M. J. and Holland, J. P. (1978) *Biochemistry* 17(23):4900-4907).

Commercially available yeast vectors include pYES2, pPIC9 (Invitrogen, San Diego, Calif.), Yepc-pADH2a, pYcDE-1 (Washington Research, Seattle, Wash.), pBC102-K22 (ATCC #67255), and YpGX265GAL4 (ATCC #67233). Mammalian cell lines including but not limited to COS-7, L cells, C127, 3T3, Chinese Hamster Ovary (CHO), HeLa, BHK, CHL-1, NSO, and HEK293 can be employed to express the recombinant antibodies in this invention. The recombinant proteins produced in mammalian cells are normally soluble and glycosylated and have authentic N-termini. Mammalian expression vectors may contain non-transcribed elements such as an origin of replication, promoter and enhancer, and 5' or 3' nontranslated sequences such as ribosome binding sites, a polyadenylation site, acceptor site and splice donor, and transcriptional termination sequences. Promoters for use in mammalian expression vectors usually are for example viral promoters such as Polyoma, Adenovirus, HTLV, Simian Virus 40 (SV 40), and human cytomegalovirus (CMV).

Depending on the expression system and host selected, a homogeneous recombinant antibody can be obtained by using various combinations of conventional chromatography used for protein purification. These include: immunoaffinity chromatography, reverse phase chromatography, cation exchange chromatography, anion exchange chromatography, hydrophobic interaction chromatography, gel filtration chromatography, and HPLC If the expression system secretes the antibody into the growth media, the protein can be purified directly from the media. If the antibody is not secreted, it is isolated from cell lysates. Cell disruption can be done by any conventional method, including freeze-thaw cycling, sonication, mechanical disruption, or use of cell lysing agents.

The plasmid construct based on pCANTAB5 (Pharmacia) was used for the bacterial expression of the single chain antibodies of this invention. For example, a plasmid containing the single chain antibody scFv(TF)3e10 is pZ612/3e10 and encodes the single chain antibody sequence followed by an e-tag sequence, which can be used to purify the protein. The amino acid sequence of the scFV(TF)3e10 antibody corresponds to SEQ ID NO:1 (Example 1), and the DNA sequence encoding scFv(TF)3e10 corresponds to SEQ ID NO:2.

The plasmid construct based on pTHR525 (see U.S. Pat. No. 5,827,824) was used for the mammalian expression of the single chain antibodies of this invention. For example, primers were designed to generate a DNA fragment spanning the pro-scFv(TF)3e10 amino acid sequence, including the N-terminal signal sequence and the C-terminal e-tag sequence, in the bacterial expression plasmid. PCR was performed to generate a DNA fragment that was inserted into the mammalian expression plasmid, which contains the ampicillin resistance gene and the hygromycin and DHFR selection markers. Expression of the single chain antibodies of the invention was driven by the MPSV LTR promoter.

In a preferred embodiment of this invention, the mammalian expression constructs were transfected into CHO DXB11 cells. Stable populations were selected using 400 µg/ml hygromycin B in HAMS/F12 medium. Expression levels were approximately 500 µg/L. To increase expression levels a population was selected using 100 nM methotrexate in alpha MEM medium. The approximate expression level of this population was 5 mg/L.

The antibodies of this invention can be purified by methods well known in the art. For example, antibodies can be affinity purified by passage over a column to which TF is bound. The bound TF-antibodies can then be eluted from the column using a buffer with a high salt concentration.

The single chain antibodies described herein contain the e-tag sequence at the C-terminus of the protein. Anti-e-tag affinity columns were purchased from American/Pharmacia Biotech. Cell culture media was filtered through a 0.22 µm filter and loaded into 5 ml e-tag column at 2 ml/min. The column was washed with 0.2 M phosphate buffer 0.05% $NaN_3$, pH 7.0, and then collected into tubes containing 0.1 volume 1M Tris buffer, pH 8.2 to neutralize the elution buffer. Alternately, the filtered culture medium was loaded onto a protein A column. In this case, the column was washed with 50 mM citric acid, 300 mM NaCl, pH 6.5 and eluted with the same buffer at pH 3.0. In both cases, the purified samples were subsequently loaded onto a Sephadex 200 column to separate monomer from dimer forms of the antibody.

Selection of Antibodies of the Invention:

Once antibodies are generated, expressed and purified, they can further characterized using BIAcore, a sTF dependent factor VIIa assay (sTF/FVIIa peptide hydrolysis assay), a FX activation assay, and the PT assay described under Example 4 in order to Identify the antibodies of this invention.

Figure 2:
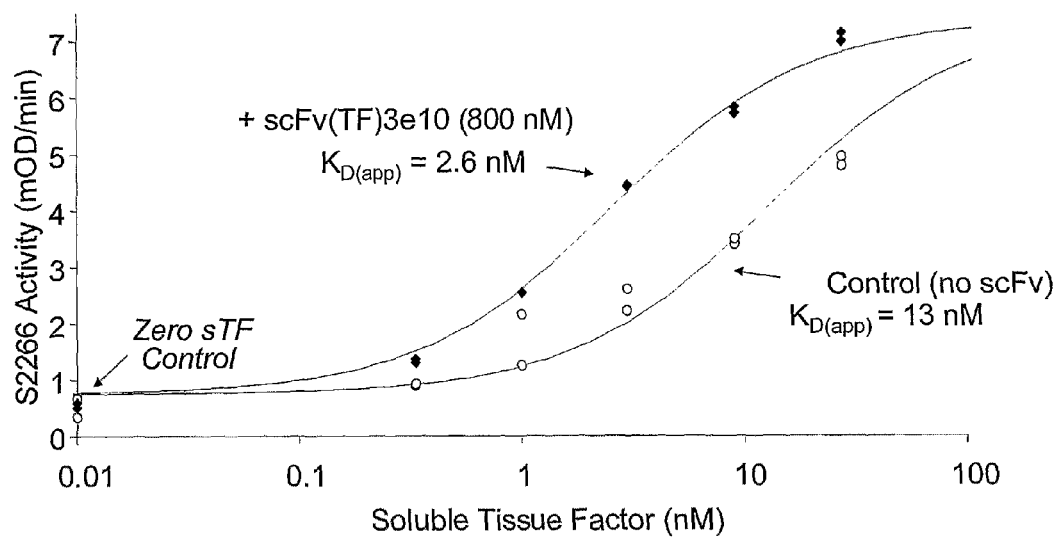
FIG. 2. Binding of scFv(TF)3e10 to sTF increases the apparent affinity of sTF for FVIIa. The sTF/FVIIa peptide hydrolysis assay was performed as described under Example 4 using 2 nM FVIIa in the presence and absence of 800 nM bacterially expressed scFv(TF)3e10. The sTF was titrated into the assay and the rate of cleavage of the chromogenic peptide substrate S2266 was determined. The $K_D$ apparent for sTF was calculated using a standard 4-parameter fit.
Figure 5:
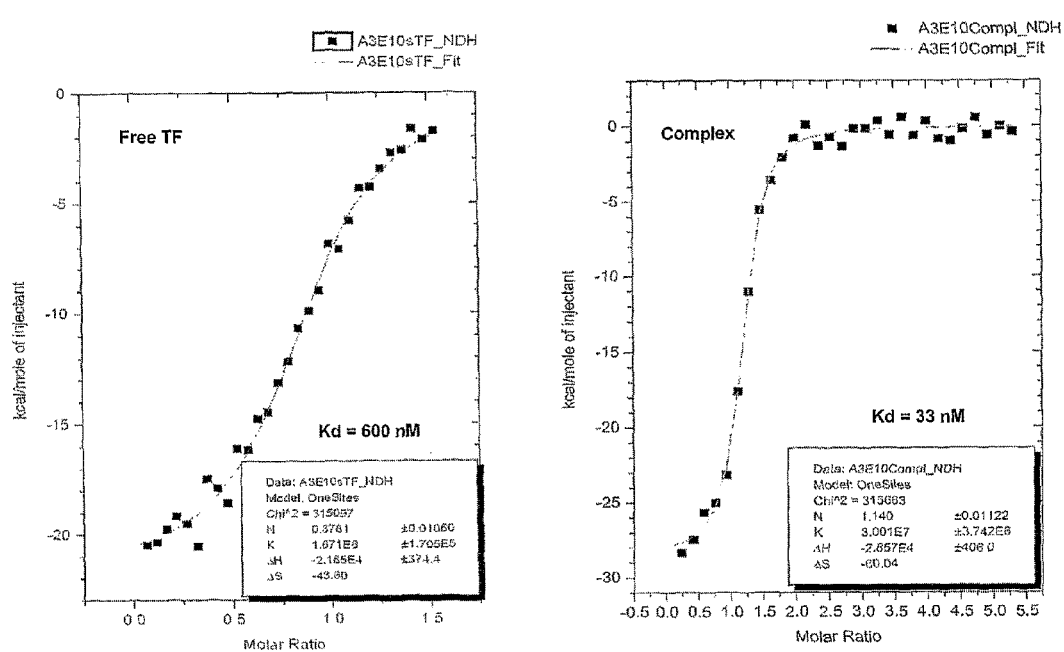
FIG. 5. Measurement of binding affinity of scFv(TF)3e10 for TF and the FVIIa/TF complex. The microcalorimetry assay was performed as described under Example 4 using scFv(TF)3e10 expressed in CHO cells. This assay shows that scFv(TF)3e10 has a ~20-fold greater affinity for the sTF/ FVIIa complex ("Complex") than for sTF ("Free TF").

In a preferred embodiment of this invention, TF-binding scFv antibodies that bind with greater affinity to the FVIIa/TF complex than to TF alone are selected using the sTF/FVIIa peptide hydrolysis assay. In this assay, TF-antibodies that bind with greater affinity to the FVIIa/TF complex than to TF are expected to increase the $K_{D(app)}$. FIG. 2 shows that the single chain antibody scFv(TF)3e10 increased the $K_{D(app)}$ ~5-fold. A microcalorimetry assay is used to measure the affinity of the TF-antibodies for the FVIIa/TF complex as compared to TF alone. FIG. 5 shows that the single chain antibody scFv(TF)3e10 has a $K_D$ of binding to the FVIIa/TF complex and free TF of 600 nM and 33 nM, respectively, which corresponds to ~20-fold greater affinity for the FVIIa/TF complex as compared to TF alone. The antibodies of this invention have at least 2-fold, preferably at least 5-fold, and more preferably at least 10-fold greater affinity for the FVIIa/TF complex than for TF.

TF-binding scFv antibodies that do not compete with FVII for binding to TF are selected using the sTF/FVIIa peptide hydrolysis assay. In this assay, TF-antibodies that compete with FVIIa for binding to TF are expected to inhibit the hydrolysis of the chromogenic substrate S2266. FIG. 1 shows that the single chain antibody scFv(TF)3e10 did not inhibit, and actually increased, FVIIa activity.

Figure 3:
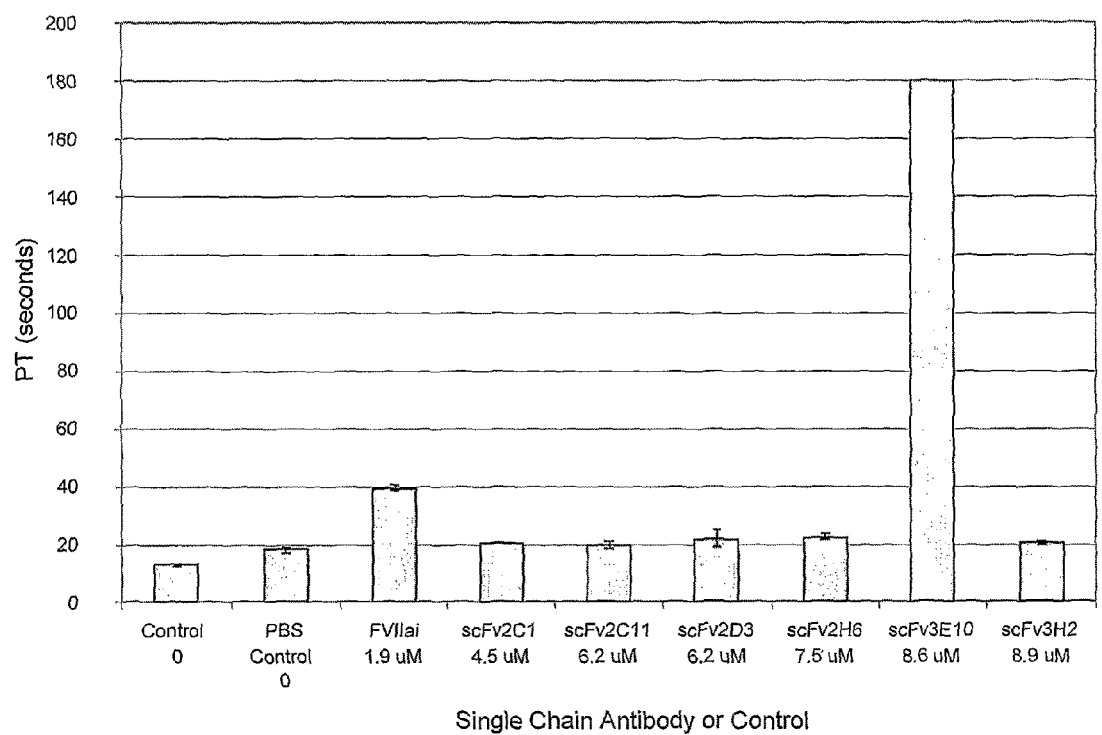
FIG. 3. Activity of TF-binding single chain antibodies in the prothrombin time (PT) assay. The PT assay was performed as described under Example 4 using recombinant human thromboplastin (Dade, Inc.) containing full length human TF in phospholipid vesicles. Final concentrations of the bacterially expressed single chain antibodies and the control protein FVIIai are indicated.
Figure 6:
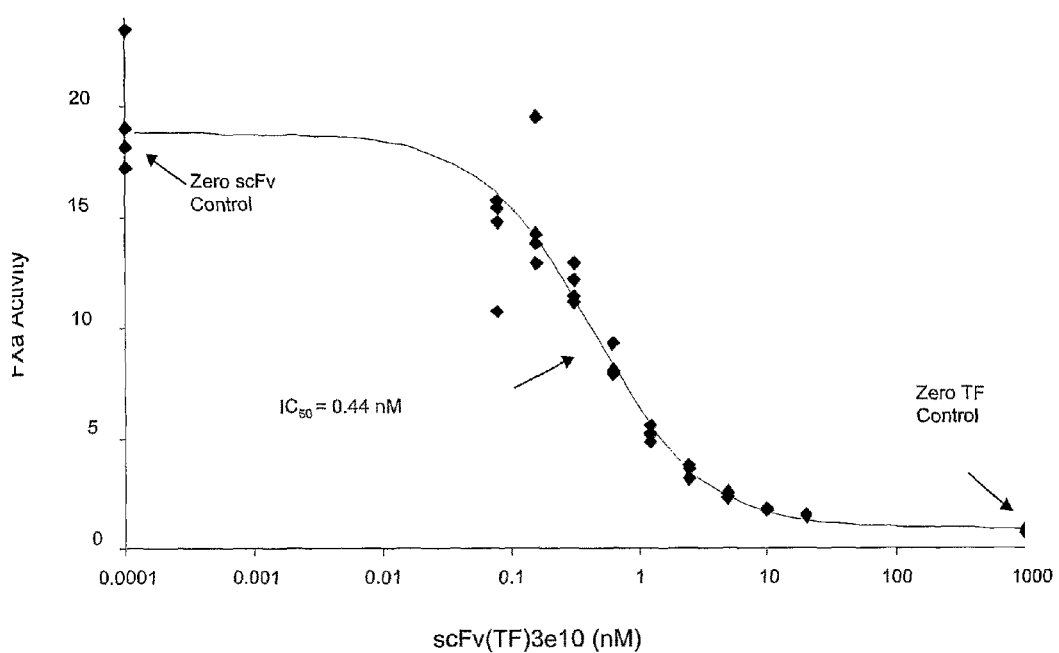
FIG. 6. scFv(TF)3e10 dose dependently inhibits FX activation. The FX activation assay was performed as described under Example 4 using increasing concentrations of bacterially expressed scFv(TF)3e10, 250 nM FX, and the FVIIa/TF complex on a phospholipid surface (10 pM FVIIa). The $IC_{50}$ represents the dose required to reach 50% maximum inhibition.

TF-binding scFv antibodies that inhibit FX activation are selected using the PT assay and the FX activation assay. In the PT assay, TF-antibodies that prolong PT are expected to inhibit FX activation. FIG. 3 shows that the single chain antibody scFv(TF)3e10 prolonged the PT, indicating that this antibody inhibits FX activation. In the FX activation assay, TF-antibodies that inhibit FXa activity are expected to inhibit the hydrolysis of the chromogenic substrate S2222. FIG. 6 shows that the single chain antibody scFV(TF)3e10 inhibited FXa activity.

Figure 7:
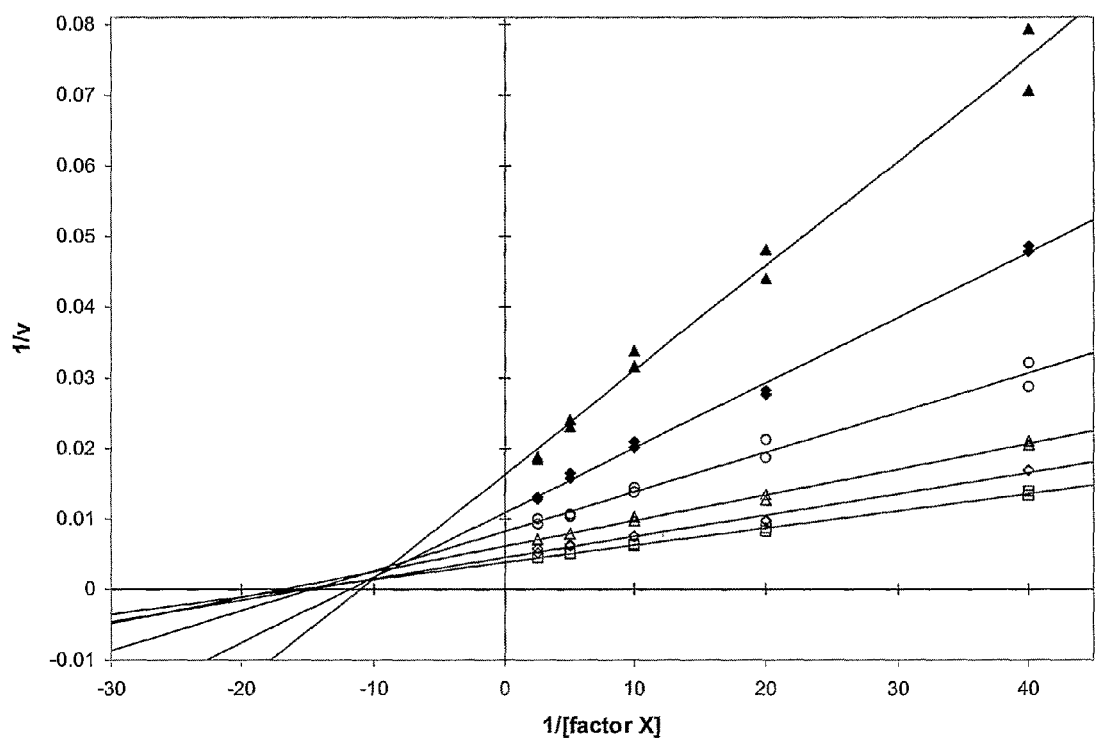
FIG. 7. scFv(TF)3e10 noncompetitively inhibits FX activation by the FVIIa/TF complex. The FX activation assay was performed as described under Example 4 using bacterially expressed scFv(TF)3e10, 25 nM to 400 nM FX, and the FVIIa/TF complex on a phospholipid surface (10 pM FVIIa). Increasing concentrations of scFv(TF)3e10 were titrated into the assay (0 nM, open square; 0.25 nM, open diamond; 0.74 nM, open triangle, 2.2 nM, open circle; 6.7 nM, filled diamond, 20 nM, filled triangle). This Lineweaver-Burk plot of (1/[S], where S (substrate)=factor X (μM); versus 1/v, where v (rate) mOD/min from S2222 hydrolysis by the FXa produced during a 5 min interval) indicates that scFv(TF)3e10 is a noncompetitive inhibitor with respect to the substrate, FX. All lines intercept on (or near) the x-axis as anticipated for a noncompetitive inhibitor (for a competitive inhibitor all lines would intercept on the y-axis).

TF-binding scFv antibodies that do not compete with FX for binding to TF are selected using the FX activation assay. In this assay, TF-antibodies that are non-competitive with FX are expected to inhibit FX activation independently from the concentration of FX used. FIG. 7 shows that the single chain antibody scFv(TF)3e10 inhibited FXa activity in a FX concentration-independent manner.

In a preferred embodiment of the present invention, a single chain antibody (scFv(TF)3e10) was identified which has a single $V_H/V_L$ binding site for TF. The amino acid sequence of scFv(TF)3e10, is shown in Example 1 and corresponds to SEQ ID NO:1. The DNA sequence encoding scFv(TF)3e10 corresponds to SEQ ID NO:2.

Analogs, Fragments, Derivatives and Variants of Antibodies of the Invention:

An analog, fragment, derivative, or variant of the antibodies of the present invention may be: (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino add residues includes a substituent group, or (iii) one in which the mature antibody is fused with another compound, such as a compound to increase the half-life of the antibody (for example, polyethylene glycol), or (iv) one in which additional amino acids are fused to the mature antibody, such as a leader or secretory sequence or a sequence which is employed for purification of the mature antibody. Such analogs, fragments, derivatives, and variants are deemed to be within the scope of those skilled in the art from the teachings herein.

Preferably, the derivatives of the present invention will contain conservative amino acid substitutions (defined further below) made at one or more predicted, preferably nonessential amino acid residues. A "nonessential" amino acid residue is a residue that can be altered from the wild-type sequence of a protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Non-conservative substitutions would not be made for conserved amino acid residues or for amino acid residues residing within a conserved protein domain, unless the substitutions were made for the purpose of selecting for variant antibodies as described further below. Fragments or biologically active portions include polypeptide fragments suitable for use as a medicament, as a research reagent, and the like. Fragments include peptides comprising amino acid sequences sufficiently similar to or derived from the amino acid sequences of an antibody of this invention and exhibiting at least one activity of that polypeptide, but which include fewer amino acids than the full-length polypeptides disclosed herein.

Moreover, preferred derivatives of the present invention include mature antibodies that have been fused with another compound, such as a compound to increase the half-life of the polypeptide and/or to reduce potential immunogenicity of the polypeptide (for example, polyethylene glycol, "PEG"). The PEG can be used to impart water solubility, size, slow rate of kidney clearance, and reduced immunogenicity to the antibody. See e.g., U.S. Pat. No. 6,214,966. In the case of PEGylations, the fusion of the antibody to PEG can be accomplished by any means known to one skilled in the art. For example, PEGylation can be accomplished by first introducing a cysteine mutation into the antibody, followed by site-specific derivatization with PEG-maleimide. The cysteine can be added to the C-terminus of the peptides. See, e.g., Tsutsumi et al. (2000) Proc. Natl. Acad. Sci. USA 97(15): 8548-8553. Another modification which can be made to the antibody involves biotinylation. In certain instances, it may be useful to have the antibody biotinylated so that it can readily react with streptavidin. Methods for biotinylation of proteins are well known in the art. Additionally, N- or O-glycosylation sites may be introduced into the antibody sequences so that post-translational N- or O-linked glycosylation of the antibodies may occur in vivo.

Variants of the antibodies of this invention include polypeptides having an amino acid sequence sufficiently similar to the amino acid sequence of the original antibodies. The term "sufficiently similar' means a first amino acid sequence that contains a sufficient or minimum number of identical or equivalent amino acid residues relative to a second amino acid sequence such that the first and second amino acid sequences have a common structural domain and/or common functional activity. For example, amino acid sequences that contain a common structural domain that is at least about 45%, preferably about 75% through 98%, identical are defined herein as sufficiently similar. Preferably, variants will be sufficiently similar to the amino acid sequence of the preferred antibodies of this invention. Variants include variants of antibodies encoded by a polynucleotide that hybridizes to a polynucleotide of this invention or a complement thereof under stringent conditions. Such variants generally retain the functional activity of the antibodies of this invention. Libraries of fragments of the polynucleotides can be used to generate a variegated population of fragments for screening and subsequent selection. For example, a library of fragments can be generated by treating a double-stranded PCR fragment of a polynucleotide with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the antibodies of this invention.

Variants include antibodies that differ in amino acid sequence due to mutagenesis. For example, mutagenesis may be performed according to recombinant DNA techniques well known in the art to modify the $V_L$ and $V_H$ domains of the Ig light and heavy chains to create variants that have increased binding affinity to the FVIIa/TF complex as compared to free TF. Particularly preferred variants include antibodies with modifications within the complementarity determining regions of the $V_L$ and $V_H$ domains.

Variants also include antibodies that differ in amino acid sequence due to the insertion or deletion of amino acid residues by mutagenesis. For example, mutagenesis may be performed according to recombinant DNA techniques well known in the art to insert or delete amino acids in the N-terminal or C-terminal portions of the $V_H$ or $V_L$ domains of the Ig light and heavy chains to create variants that retain substantially similar functional activity. Particularly preferred variants include single chain antibodies with insertions or deletions of amino acid residues in the $V_H$-$V_L$ linker between the $V_H$ and $V_L$ domains. The $V_H$-$V_L$ linker sequence in the single chain antibody depicted in Example 1 is 5 amino acid residues in length. It will be apparent that other short linker sequences, from 0 to 20 amino acids may be used, wherein the antibody retains substantially similar functional activity. Modifications of the existing $V_H$-$V_L$ linker may be aimed at increasing the stability of the dimer form of the single chain antibody.

In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential variant amino acid sequences is expressible as individual polypeptides, or, alternately, as a set of larger fusion proteins (for example, for phage display) containing the set of sequences therein. There are a variety of methods that can be used to produce libraries of potential variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential variant sequences. Methods for synthesizing degenerate oligonucleotides are known in the art (see, e.g., Narang (1983) *Tetrahedron* 39:3; Itakura et al. (1984a) *Annu. Rev. Biochem.* 53:323; Itakura et al. (1984b) *Science* 198:1056; Ike et al. (1983) *Nucleic Acid Res.* 11:477).

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of antibodies for TF- or FVIIa/TF complex-binding activity or FX activation inhibitory activity. The most widely used techniques, which are amenable to high throughput analysis for screening large gene libraries typically Include cloning the gene library into replicable expression vectors, transforming appropriate cells with the resulting library of vectors and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify the desired variants.

Example 1 depicts the amino acid sequence of one TF-binding single chain antibody, scFv(TF)3e10 (SEQ ID NO:1), and delineates the $V_H$-$V_L$ linker and the $V_H$ and $V_L$ domains. Variants that have TF- or FVIIa/TF complex-binding activity or inhibit FX activation can be identified by screening combinatorial libraries of mutants, for example insertion, truncation or point mutants, of the antibodies of this invention using the sTF/FVIIa peptide hydrolysis or FX activation assays described in Example 4. The antibodies of the present invention include the antibodies of Example 1 and 3 (SEQ ID NOs:1 and 3), as well as those antibodies having insubstantial variations in sequence from it. An "insubstantial variation" would include any sequence, substitution, or deletion variant that maintains substantially at least one biological function of the antibodies of this invention, e.g., the ability to inhibit FX activation. These functional equivalents may preferably include antibodies which have at least about a 90% identity to the $V_L$ or $V_H$ region domains of the single chain antibody of SEQ ID NO:1 or SEQ ID NO:3, and more preferably at least a 95% identity to the $V_L$ or $V_H$ region domains of the single chain antibody of SEQ ID NO:1 or SEQ ID NO:3, and still more preferably at least a 97% identity to the $V_L$ or $V_H$ region domains of the single chain antibody of SEQ ID NO:1 or SEQ ID NO:3, and also include portions of such antibody having substantially the same biological activity. However, any antibody having insubstantial variation in amino acid sequence from the antibody of SEQ ID NO:1 or SEQ ID NO:3 that demonstrates functional equivalency as described further herein is included in the description of the present invention.

Pharmaceutical Compositions:

The invention also provides pharmaceutical compositions which can be administered to a patient to achieve a therapeutic effect. Pharmaceutical compositions of this invention can be prepared for administration by combining the antibody of this invention having the desired degree of purity and the pharmaceutically effective amount with physiologically acceptable carriers.

The antibodies of the present invention can be used in pharmaceutical compositions, for intravenous administration or subcutaneous administration or intrathecal administration. Thus, the above described antibodies preferably will be combined with an acceptable sterile pharmaceutical carrier, such as five percent dextrose, lactated Ringer's solution, normal saline, sterile water, or any other commercially prepared physiological buffer solution designed for intravenous infusion. It will be understood that the selection of the carrier solution and the dosage and administration of the composition will vary with the subject and the particular clinical setting, and will be governed by standard medical procedures.

In accordance with the methods of the present invention, these pharmaceutical compositions may be administered in amounts effective to inhibit the pathological consequences associated with excess thrombin generation in the subject.

Administration of the antibody may be by a bolus intravenous injection, by a constant intravenous infusion or by a combination of both routes. Alternatively, or in addition, the antibody mixed with appropriate excipients may be taken into the circulation from an intramuscular site. Systemic treatment with antibody can be monitored by determining the activated partial thromboplastin time (PT) on serial samples of blood taken from patient. The coagulation time observed in this assay is prolonged when a sufficient level of the antibody is achieved in the circulation.

The recombinant antibodies and pharmaceutical compositions of this invention are useful for parenteral, topical, intravenous, oral or local administration. The pharmaceutical compositions can be administered in a variety of unit dosage forms depending upon the method of administration. For example, unit dosage forms can be administered in the form including but not limited to tablets, capsules, powder, solutions, and emulsions.

The recombinant antibodies and pharmaceutical compositions of this invention are particularly useful for intravenous administration. The compositions for administration will commonly comprise a solution of the single chain antibody dissolved in a pharmaceutically acceptable carrier, preferably in an aqueous carrier. A variety of aqueous carriers can be used, e.g., buffered saline and the like. These solutions are sterile and generally free of undesirable matter. The compositions may be sterilized by conventional, well known sterilization techniques.

A typical pharmaceutical composition for intravenous administration can be readily determined by one of ordinary skill in the art. The amounts administered are clearly protein specific and depend on its potency and pharmacokinetic profile. Actual methods for preparing parenterally administrable compositions will be known or apparent to those skilled in the art and are described in more detail in such publications as *Remington's Pharmaceutical Science*, 15$^{th}$ ed., Mack Publishing Company, Easton, Pa. (1980).

The compositions containing the present antibodies of the invention or a cocktail thereof (i.e., with other proteins) can be administered as therapeutic treatments. In therapeutic applications, compositions are administered to a patient suffering from a bleeding disorder or disease in an amount sufficient to cure or at least partially arrest the bleeding. An amount adequate to accomplish this is defined as a "therapeutically effective amount". Amounts effective for this use will depend upon the severity of the disease and the general state of the patient's health.

Single or multiple administration of the compositions may be administered depending on the dosage and frequency as required and tolerated by the patient. In any event, the composition should provide a sufficient quantity of the proteins of this invention to effectively treat the patient.

The antibodies of the invention, or their pharmaceutically acceptable compositions, are administered in a therapeutically effective amount, which will vary depending upon a variety of factors including the activity of the specific antibody employed; the metabolic stability and length of action of the antibody; the age, body weight, general health, sex, and diet of the patient; the mode and time of administration; the rate of excretion; the drug combination; the severity of the particular disease-states; and the host undergoing therapy. Generally, a daily therapeutically effective amount is from about 0.14 mg to about 14.3 mg/kg of body weight per day of an antibody of the invention, or a pharmaceutically acceptable composition thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of an antibody of the invention, or a pharmaceutically acceptable composition thereof, preferably from about 50 mg to about 700 mg per day, and most preferably from about 100 mg to about 500 mg per day.

Cell and Gene Therapy:

An antibody of the invention may be employed in accordance with the present invention by expression of such antibody in vivo by a method referred to as "cell therapy". Thus, for example, cells may be engineered with a polynucleotide (DNA or RNA) encoding the antibody ex vivo, and the engineered cells are then provided to a patient to be treated with the antibody. Such methods are well known in the art. For example, cells may be engineered by procedures known in the art by use of a retroviral particle containing RNA encoding the antibody of the present invention.

An antibody of the invention may also be employed in accordance with the present invention by expression of such antibody in vivo by a method referred to as "gene therapy". Thus, for example, a virus may be engineered with a polynucleotide (DNA or RNA) encoding the antibody, and the engineered virus is then provided to a patient to be treated with the antibody. Such methods are well known in the art. For example, recombinant adenoviruses may be engineered by procedures known in the art containing DNA encoding the antibody of the present invention.

Local delivery of the anticoagulant antibodies of the present invention using cell or gene therapy may provide the therapeutic agent to the target area, the endothelial cells lining blood vessels.

Both in vitro and in vivo cell and gene therapy methodologies are contemplated. Several methods for transferring potentially therapeutic genes to defined cell populations are known. See, e.g., Mulligan (1993) *Science* 260:926-931. These methods include:

1) Direct gene transfer. Se, e.g., Wolff et al. (1990) *Science* 247: 1465-1468;
2) Liposome-mediated DNA transfer. See, e.g., Caplen et al. (1995) *Nature Med.* 3:3% 46; Crystal (1995) *Nature Med.* 1:15-17; Gao and Huang (1991) *Biochem. Biophys. Res. Comm.* 179:280-285;
3) Retrovirus-mediated DNA transfer. See, e.g., Kay et al. (1993) *Science* 262:117-119; Anderson (1992) *Science* 256:808-813.
4) DNA Virus-mediated DNA transfer. Such DNA viruses include adenoviruses (preferably Ad2 or Ad5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al. (1994) *Gene Therapy* 1:367-384; U.S. Pat. No. 4,797, 368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity. However, recent developments in the field of lentiviral vectors may circumvent some of these limitations. See Naldini et al. (1996) *Science* 272:263-267.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Adenoviruses have the advantage that they have a broad host range, can infect quiescent or terminally differentiated cells, such as neurons or hepatocytes, and appear essentially non-oncogenic. See, e.g., Ali et al. (1994), supra, p. 367. Adenoviruses do not appear to integrate into the host genome. Because they exist extrachromosomally, the risk of insertional mutagenesis is greatly reduced. Ali et al. (1994), supra, p. 373.

Adeno-associated viruses exhibit similar advantages as adenoviral-based vectors. However, AAVs exhibit site-specific integration on human chromosome 19 (Ali et al. (1994), supra, p. 377).

In a preferred embodiment, the DNA encoding the antibodies of this invention is used in cell or gene therapy for disorders including, but not limited to, deep vein thrombosis, disseminated intravascular coagulation, acute coronary syndrome or cancer with evidence of coagulopathy.

According to this embodiment, cell or gene therapy with DNA encoding the antibodies of this invention is provided to a patient in need thereof, concurrent with, or immediately after diagnosis.

The skilled artisan will appreciate that any suitable gene therapy vector containing DNA encoding the antibody of the invention or DNA encoding analogs, fragments, derivatives or variants of the antibody of the invention may be used in accordance with this embodiment. The techniques for constructing such a vector are known. See, e.g., Anderson, W. F. (1998) *Nature* 392:25-30; Verma I. M. and Somia, N. (1998) *Nature* 389:239-242. Introduction of the antibody DNA-containing vector to the target site may be accomplished using known techniques.

The cell or gene therapy vector includes one or more promoters. Suitable promoters which may be employed include, but are not limited to, the retroviral LTR; the SV40 promoter; and the human cytomegalovirus (CMV) promoter described in Miller et al. (1989) *Biotechniques* 7(9):980-990, or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the antibody of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter, inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter, and human growth hormone promoter.

The retroviral plasmid vector is employed to transduce packaging cell lines to form producer cell lines. Examples of packaging cells which maybe transfected include, but are not limited to, the PE501, PA317, ψ-2, ψ-AM, PA12, T19-14X; VT-19-17-H2, ψCRE, ψCRIP, GP+#-86, GP+envAm12, and DAN cell lines as described in Miller (1990) *Human Gene Therapy* 1:5-14, which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host. The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

A different approach to gene therapy is "transkaryotic therapy" wherein the patient's cells are treated ex vivo to induce the dormant chromosomal genes to produce the protein of interest after reintroduction to the patient. Transkaryotic therapy assumes the individual has a normal complement of genes necessary for activation. Transkaryotic therapy involves introducing a promoter or other exogenous regulatory sequence capable of activating the nascent genes, into the chromosomal DNA of the patients' cells ex vivo, culturing and selecting for active protein-producing cells, and then reintroducing the activated cells into the patient with the intent that they then become fully established. The "gene activated" cells then manufacture the protein of interest for some significant amount of time, perhaps for as long as the life of the patient. U.S. Pat. Nos. 5,641,670 and 5,733,761 disclose in detail this concept, and are hereby incorporated by reference in their entirety.

Kits:

This invention further relates to kits for research or diagnostic purposes. Kits typically include one or more containers containing the antibodies of the present invention. In a preferred embodiment, the kits comprise containers containing single chain antibodies in a form suitable for derivatizing with a second molecule. In a more preferred embodiment the kits comprise containers containing the antibody of SEQ ID NO:1 or SEQ ID NO:3.

In another embodiment, the kits may contain DNA sequences encoding the antibodies of the invention. Preferably the DNA sequences encoding these antibodies are provided in a plasmid suitable for transfection into and expression by a host cell. The plasmid may contain a promoter (often an inducible promoter) to regulate expression of the DNA in the host cell. The plasmid may also contain appropriate restriction sites to facilitate the insertion of other DNA sequences into the plasmid to produce various antibodies. The plasmids may also contain numerous other elements to facilitate cloning and expression of the encoded proteins. Such elements are well known to those of skill in the art and Include, for example, selectable markers, initiation codons, termination codons, and the like. In a more preferred embodiment the kits comprise containers containing the DNA sequences of SEQ ID NO:2 or SEQ ID NO:4.

Therapeutic Indications:

Diseases in which thrombus formation play a significant etiological role include myocardial infarction, disseminated intravascular coagulation, deep vein thrombosis, pulmonary embolism, ischaemic stroke, septic shock, acute respiratory distress syndrome, unstable angina and other arterial and venous occlusive conditions. The antibodies of this invention are useful in all of these, as well as in other diseases in which thrombus formation is pathological. Other pathological conditions where the antibody of this invention may be useful include cancer with coagulopathy and inflammation. The antibodies may also find use in skin and vein grafts and organ transplants. By useful it is meant that the antibodies are useful for treatment, either to prevent disease or to prevent its progression to a more severe state. The antibodies of this invention also provide a safe and effective anticoagulant, for example, in patients receiving bioprostheses such as heart valves. These antibodies may replace heparin and warfarin in the treatment of, for example, pulmonary embolism or acute myocardial infarction. The antibodies of this invention may also find use in coating medical devices where coagulation is an issue of concern.

Assays:

A number of laboratory assays for measuring the in vitro anticoagulant activity of an antibody of this invention are available. The anticoagulant effect of an antibody can be measured using plasma clotting time assays such as the activated partial thromboplastin time ("APTT"), thrombin clotting time ("TCT") and/or prothrombin time ("PT"). These assays distinguish between different mechanisms of coagulation inhibition, and involve the activation of protein C. Prolongation of the clotting time in any one of these assays demonstrates that the molecule can inhibit coagulation in plasma.

The above assays are used to identify antibodies with anticoagulant activity which are able to bind TF in both purified systems and in a plasma milieu. Further assays are then used to evaluate other activities of the antibodies of the invention, such as inhibition of thrombin catalyzed formation of fibrin from fibrinogen (Jakubowski, H. V. et al. (1986) *J. Biol. Chem.* 261(8): 3876-3882), Inhibition of thrombin activation of factor V (Esmon, C. T. et al. (1982). *J. Biol. Chem.* 257 (14):7944-7947), accelerated inhibition of thrombin by antithrombin III and heparin cofactor II (Esmon, N. L. et al. (1983) *J. Biol. Chem.* 258(20):12238-12242), inhibition of thrombin activation of factor XIII (Polgar, J. et al. (1987) *Thromb. Haemost.* 58(1):140), inhibition of thrombin mediated inactivation of protein S (Thompson, E. A. and Salem, H. H. (198.6) *J. Clin. Inv.* 78(1):13-17), and inhibition of thrombin mediated platelet activation and aggregation (Esmon, N. L. et al. (1983), supra).

The following assays, described in detail under Example 4, are used to measure the in vitro potency or the in vitro binding affinity of the antibodies of the Invention: 1) sTF/FVIIa peptide hydrolysis assay; 2) factor X activation assay; 3) PT assay; and 4) microcalorimetry assay.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical results. Those of skill in the art will have sufficient knowledge of such systems and methodologies so as to be able, without undue experimentation, to make such substitutions as will optimally serve their purposes in using the methods and procedures disclosed herein.

The present invention will now be further described by the following non-limiting examples as a guide to assist in the practice of the invention. In applying the disclosure of the example it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius and, all parts and percentages are by weight, unless otherwise indicated.

The entire disclosure(s) of all applications, patents and publications, cited above are hereby incorporated by reference.

EXAMPLE 1

Single Chain Anti-TF Antibody Construct ScFv(TF)3e10

```
(-18) M L G V L V G A L A L A G L V F P E M A Q
      V N L R E S G G T L V Q P G G S L R L S C A A S
      G F S F T D A W M S W V R Q A P G K E L E W V S
      S I S G S G G S T Y Y A G S V K G R F T I S R D
      N S K N T L Y L Q M N S L R A E D T A V Y Y C A
      R V L S L T D Y Y W Y G M D V W G Q G T L V T V
      S A G G G G S G A P N F M L T Q P H S V S A S P
      G K T V T I S C T R S S G S V A S Y Y V Q W Y Q
      Q R P G S S P T T V I Y E D N H R P S G V P D R
      F S G S I D T S S N S A S L T I S G L K T E D E
      A D Y Y C Q S Y D S N N L V V F G G G T K L T V
      L G A A A G A P V P Y P D P L E P R A A (264)
```

The single chain anti-TF antibody scFv(TF)3e10 (SEQ ID NO:1) consists of a signal peptide (−18 to −1), $V_H$ domain (1 to 126), $V_H$-$V_L$ linker (127 to 131), $V_L$ domain (132 to 246), and e-tag sequence (247 to 264). The scFv(TF)3e10 DNA sequence (SEQ ID NO:2) encodes the amino acid sequence of SEQ ID NO:1.

EXAMPLE 2

Single Chain Anti-TF Antibody Construct scFv(TF)3e10Δ

```
(-18) M L G V L V L G A L A L A G L V F P E M A Q
      V N L R E S G G T L V Q P G G S L R L S C A A S
      G F S F T D A W M S W V R Q A P G K E L E W V S
      S I S G S G G S T Y Y A G S V K G R F T I S R D
      N S K N T L Y L Q M N S L R A E D T A V Y Y C A
      R V L S L T D Y Y W Y G M D V W G Q G T L V T V
      S A G G G G S N F M L T Q P H S V S A S P G K T
      V T I S C T R S S G S V A S Y Y V Q W Y Q Q R P
      G S S P T T V I Y E D N H R P S G V P D R F S G
      S I D T S S N S A S L T I S G L K T E D E A D Y
      Y C Q S Y D S N N L V V F G G G T K L T V L G A
      A A G A P V P Y P D P L E P R A A (243)
```

The single chain anti-TF antibody scFv(TF)3e10Δ (SEQ ID NO:3) consists of a signal peptide (−18 to −1), $V_H$ domain (1 to 126), $V_H$-$V_L$ linker (127 to 131), and $V_L$ domain (132 to 243). scFv(TF)3e10Δ differs from scFv(TF)3e10 by deletion of 3 amino acids (GAP) at the N-terminus of the $V_L$ domain and by deletion of the C-terminal e-tag sequence. The scFv (TF)3e10Δ DNA sequence (SEQ ID NO:4) encodes the amino acid sequence of SEQ ID NO:3.

EXAMPLE 3

Expression of the Anti-TF Antibodies in Bacterial and Mammalian Cells

Six different single chain antibodies, scFv(TF)2c1, scFv (TF)2c11, scFv(TF)2d3, scFv(TF)2h6, scFv(TF)3e10 and scFv(TF)3h2, were identified from TF-binding phage, overexpressed in *E. coli*, and affinity purified using an e-tag affinity column as described above. The affinities of the six purified antibodies for sTF were measured using BIAcore, and then these antibodies were characterized in the sTF/FVIIa peptide hydrolysis, FX activation, PT, and microcalorimetry assays described under Example 4, the results of which are described under Example 5.

The scFv(TF)3e10 antibody (SEQ ID NO: 1) was also expressed in CHO cells. The expression plasmid contained the DNA sequence encoding scFV(TF)3e10 (SEQ ID NO:2) and both the hygromycin B and DHFR selection markers. Original selection was done in 400 μg/ml hygromycin to select a population. The resulting population was then subjected to 100 nM methotrexate selection. During this selection, cells that have amplified copies of the region of DNA containing the selection marker, and target gene, are selected from amongst the population. The expression levels were increased from approximately 0.3 mg/L to about 6 mg/L as a result of this selection.

EXAMPLE 4

In Vitro Potency and Binding Affinity Assays 1. sTF/FVIIa Peptide Hydrolysis Assay The principle of this assay is depicted below. The tripeptide p-nitroanilide amide bond of the substrate is hydrolyzed by the sTF/FVIIa complex. The liberated chromophore product, p-nitroanilide, is monitored at 405 nm and the concentration of product formed per unit time is calculated using a molar extinction coefficient of 9920 $M^{-1}$ $cm^{-1}$. $IC_{50}$ values (C) are determined by fitting the initial rates into the 4 parameter equation: $Y=(A-D)/(1+(x/C)^B)+D$

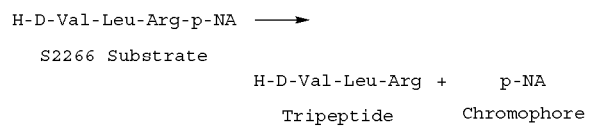

Reagents and Solutions:
1. Assay buffer: 50 mM Tris-HCl, 150 mM NaCl, 5 mM $CaCl_2$, 0.1% BSA, pH7.5
2. Human FVIIa (HCVIIA-0060, Haematologic Technologies Inc.): 10× working solution—prepare 20 nM solution in assay buffer prior to use.
3. Soluble TF (Berlex): 10× working solution—prepare 30 nM solution in assay buffer prior to use.
4. Chromogenic substrate S2266 (Kabi Pharmacia Hepar Inc.): Stock solution: 10 mM in $H_2O$, stored at 4 C. 2.5× working solution—prepare 2.5 mM solution in assay buffer prior to use.
5. Antibody: Prepare 2.5× dilutions in assay buffer prior to use.

Assay Conditions:
Assays are performed in a 96-well microtiter plate at room temperature. The final concentrations of the components are as follows:

| sTF | 3 nM |
| --- | --- |
| Antibody | vary from 1000 to 0.625 nM |
| FVIIa | 2 nM |
| S2266 | 1 mM |

Assay Procedure:
1. Pipette 0.1 ml of 2.5× AB (or buffer control) into each well.
2. Add 0.025 ml 10× sTF and incubate 10 min at room temperature with mild shaking.
3. Add 0.025 ml 10× FVIIa, incubate 10 min at room temperature with mild shaking.
4. Add 0.1 ml 2.5× S2266 substrate, immediately transfer the plate into a plate reader and measure enzyme kinetics at 405 nm at 10 seconds interval for 15 min.

This assay may be used to measure an apparent $K_D$ of binding of the antibodies of the invention to sTF or the FVIIa/TF complex, and to determine whether the antibodies of the invention compete with FVII for binding to TF.

2. Factor X Activation Assay

The principle of this assay is depicted below. FVIIa is incubated with recombinant human TF vesicles to form a protease complex capable of activating the substrate, FX. This complex is formed in the presence (or absence) of different concentrations of antibody, then the substrate FX is introduced and the reaction is allowed to proceed to form the product, active protease FXa, which is capable of hydrolyzing the p-nitroanilide amide bond of the chromogenic substrate S2222. The liberated chromophore product, p-nitroanilide, is monitored at 405 nm and the concentration of product formed per unit time is calculated using a molar extinction coefficient of 9920 $M^{-1}cm^{-1}$. $IC_{50}$ values (C) are determined by fitting the initial rates into the 4-parameter equation: $Y=(A-D)/(1+(x/C)^B)+D$

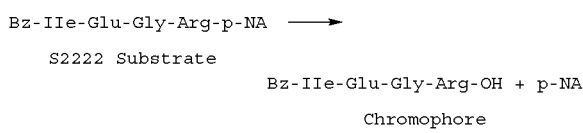

Reagents and Solutions:

1. Assay buffer: 50 mM Tris-HCl, 150 mM NaCl, 5 mM $CaCl_2$, 0.1% BSA, pH7.5
2. Human FVIIa (HCVIIA-0031, Haematologic Technologies Inc.): 4× working solution—prepare 100 pM solution in assay buffer prior to use.
3. Recombinant Human TF (reconstituted in our lab from Innovin, Dade): working solution—prepare 1:480 dilution in assay buffer prior to use.
4. Human factor X (HCX-0060, Haematologic Technologies Inc.): 4× working solution—prepare 1000 nM solution in assay buffer prior to use.
5. Chromogenic substrate S2222 (Kabi Pharmacia Hepar Inc.):

Stock solution: 6 mM in $H_2O$, stored at 4 C.

Working solution—prepare 0.78 mM solution in 3.57 mM EDTA (to stop the reaction), 150 mM NaCl, 50 mM Tris-HCl pH 7.5 prior to use.

6. Antibody:

Prepare 4× dilutions in assay buffer prior to use.

Assay Conditions:

Assays are performed in a 96-well microtiter plate at room temperature. The final concentrations of the components are as follows:

| rTF vesicles | ¼ of 1:480 dilution |
| --- | --- |
| Antibody | vary from 1000 to 0.625 nM |
| FVIIa | 25 pM |
| FX | 250 nM |
| S2222 | 0.546 mM |

Assay Procedure:
1. Pipette 0.015 ml of 4×AB (or buffer control) into each well.
2. Add 0.015 ml 4× rTF vesicles.
3. Add 0.015 ml 4× FVIIa, incubate 10 min at room temperature with mild shaking.
4. Add 0.015 ml 4× FX, incubate 5 min at room temperature with mild shaking.
5. Add 0.14 ml S2222 substrate, immediately transfer the plate into a plate reader and measure enzyme kinetics at 405 nm at 10 seconds interval for 15 minutes.

This assay may be used to determine whether the antibodies of the invention inhibit the FVIIa/TF complex to activate FX, and to determine whether the antibodies of the invention compete with FX for binding to the FVIIa/TF complex.

3. Prothrombin Time (PT) Assay

For the standard PT reaction, 90l of an appropriate concentration of the antibody or PBS is added to 20 µl Thromboplastin IS (Dade) and 90 µl of 25 mM $CaCl_2$ in a cuvette. The mixture is incubated for 1 min at 37° C., then 100 µl of citrated plasma (Helena Laboratories). Alternatively, an appropriate volume of concentrated antibody is added to 100 µl of recombinant human thromboplastin (Ortho Recombiplastin) and approximately 2 min later, 100 µl reconstituted human plasma is added. Clotting time for each individual coagulation assay is measured by taking the average of two measurements using an Electra 900C Coagulometer (Hemoliance) and the average values determined from replicate assays (n=3 or 4). Dose response curves were generated for each inhibitor and then regression analysis was used to calculate the concentration (in nM) necessary for a two-fold extension of the clotting time.

This assay may be used to evaluate the effect of the antibodies of the invention on the extrinsic blood coagulation pathway. The amount of antibody required to double the PT is determined, and may be compare to other anticoagulants to assess the relative potency of the antibodies of the invention.

4. Microcalorimetry Assay

The microcalorimetry (isothermal titration calorimetry) assay is used to measure the binding affinity ($K_D$) of the antibodies of the invention to TF alone or the FVIIa/TF complex. This assay is performed using a MicroCal VP-ITC instrument. The FVIIa/TF complex is preformed by adding a 2.3 fold molar excess of FVIIai to sTF. Size exclusion chromatography is used to verify that the sTF in the assay is completely complexed. For determination of the antibody affinity for the complex, 1.2 µM VIIa/TF complex is added to the microcalorimeter cell and 65 µM antibody is added to the syringe. For determination of the antibody affinity for sTF alone, 10 µM sTF is added to the cell and 141 µM antibody is added to the syringe. Data analysis is performed using MicroCal Origin software. The data is fit to a single binding site.

EXAMPLE 5

In Vitro Characteristics of the Anti-TF Antibodies of this Invention

Figure 4:
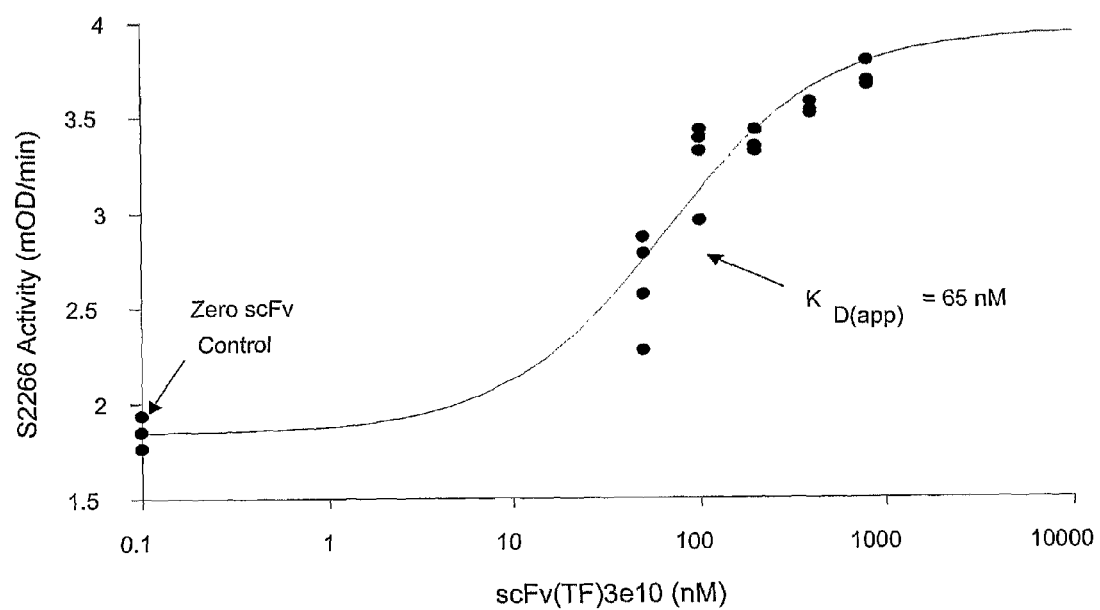
FIG. 4. Measurement of apparent binding affinity of scFv (TF)3e10 for sTF. The sTF/FVIIa peptide hydrolysis assay was performed as described under Example 4 using 3 nM sTF and 2 nM FVIIa. The concentration of sTF used was below the $K_D$ for binding to FVIIa. Bacterially expressed scFv(TF)3e10 was added at increasing concentrations and the increased rate of reaction was used to determine the $K_D$ apparent of this antibody for sTF using a standard 4-parameter fit. The affinity of scFv(TF)3e10 for the sTF/FVIIa complex ($K_{D(app)}$=65 nM) is greater than the affinity of scFv(TF) 3e10 for sTF measured using BIAcore ($K_{D(app)}$=470 nM).

Six different TF-binding antibodies were isolated from a fully human single chain antibody phage display library: scFv(TF)2c1, scFv(TF)2c11, scFv(TF)2d3, scFv(TF)2h6, scFv(TF)$_3$e10 and scFv(TF)3h2. The affinities of these sTF-binding antibodies, expressed in *E. coli*, as measured using the BIAcore, were between 35 and 470 nM. The sTF/VIIa peptide hydrolysis assay described under Example 4 was used to determine if these antibodies blocked the formation of an active VIIa/TF complex. In this assay, binding of VIIa to sTF accelerates the rate of cleavage against the chromogenic peptide substrate S2266 by >20-fold. Antibodies that inhibit binding of FVIIa to TF block this acceleration. Five of the single chain antibodies, scFv(TF)2c1, scFv(TF)2c11, scFv(TF)2d3, scFv(TF)2h6, and scFv(TF)3h2, inhibited S2266 hydrolysis, suggesting that they inhibit FVIIa binding to sTF (FIG. 1). In contrast, the single chain antibody scFv(TF)3e10 did not inhibit the sTF/VIIa peptide hydrolysis assay and, in fact, this antibody increased the rate of S2266 hydrolysis, suggesting that scFv(TF)3e10 increases the affinity of sTF for FVIIa. Using the sTF/VIIa peptide hydrolysis assay, the scFv(TF)3e10 antibody increased the affinity of FVIIa for sTF, decreasing the $K_D$ apparent 5-fold (FIG. 2). scFv(TF)3e10 did not affect the rate of hydrolysis by FVIIa in the absence of sTF, indicating that this antibody does not interact with FVIIa alone. The $K_D$ of the scFv(TF)3e10 antibody for sTF, measured using the sTF/FVIIa peptide hydrolysis assay, was 65.4 nM (FIG. 4). A microcalorimetry assay was used to compare the affinity of scFv(TF)3e10 for TF as compared to the FVIIa/TF complex. These experiments revealed that mammalian cell expressed scFv(TF)3e10 has a ~20-fold higher affinity for the TF/FVIIa complex as compared to free sTF (33 nM vs. 600 nM, FIG. 5).

The six TF-binding single chain antibodies, expressed in bacteria, were compared using the FX activation assay and the PT assay. None of the five antibodies that inhibited the rate of S2266 hydrolysis by the sTF/FVIIa complex, scFv(TF)2c1, scFv(TF)2c11, scFv(TF)2d3, scFv(TF)2h6, and scFv(TF)3h2, extended the PT beyond the PBS buffer control (FIG. 3). In contrast, although the scFv(TF)3e10 antibody did not have the highest affinity as measured by BIAcore, and it increased the affinity of FVIIa for sTF, scFv(TF)3e10 was the only antibody in the group that inhibited FX activation (FIG. 6 and data not shown) and prolonged clotting time in the PT assay (FIG. 3). The $IC_{50}$ of the scFv(TF)3e10 (dimer) antibody for inhibition in the FX activation assay was 0.44 nM (FIG. 6). Finally, the FX activation assay was used to determiner whether the scFv(TF)3e10 antibody competes with FX for binding to the FVIIa/TF complex. scFv(TF)3e10 dose dependently inhibited FX activation with the same $K_{D(app)}$ at all concentrations of the substrate FX, indicating that scFv(TF)3e10 is noncompetitive with FX and does not bind to TF or to the FVIIa/TF complex at the same site as FX (FIG. 7).

The scFv(TF)3e10 antibody was identified on the basis of binding to recombinant human soluble TF. The sequence homology of TF between the human and murine or human and rabbit is 58% and 71%, respectively. The antibody appears to bind to a unique epitope on human TF that interferes with activation of FX by the FVIIa/TF complex. Physiologically, this antibody has an advantage over antibodies that compete with FVII or FVIIa binding to TF. The $K_D$ of FVIIa for soluble TF is ~10 nM (FIG. 2), a value that is consistent with published values for the binding of FVIIa to sTF (4.8 nM, Neuenschwander, P. F. and Morrissey, J. H. (1994) *J. Biol. Chem.* 269(11):8007-8013) or the binding of FVII, FVIIa and DIP inactivated-FVIIai to full length TF reconstituted in neutral phosphatidylcholine vesicles (Bach R. et al. (1986) *Biochemistry* 25:4007-4020). The affinity of FVII or FVIIa binding to full length TF increases greatly when charged phosphatidyl serine is included in the phospholipid vesicles (Bach R. et al. (1986) supra), due to the interaction of the GLA domain of FVII or FVIIa with the charged membrane surface (Neuenschwander, P. F. and Morrissey, J. H. (1994) supra). Under these optimal conditions, the FVIIa binds to full length TF with a very high affinity (41 pM). A TF antibody that competes with FVII or FVIIa binding will have difficulty competing for this high affinity FVIIa/TF complex. In contrast, the scFv(TF)3e10 antibody not only has greater affinity for the FVIIa/TF complex than to TF, but it does not compete with FVIIa for binding to TF. An antibody such as scFv(TF)3e10, which does not compete with FVIIa, will inhibit the activation of FX independent of the plasma concentration of FVII, which is ~10 nM.

The scFv(TF)3e10 antibody also has an advantage over antibodies that compete with FX for binding to TF. The $K_m$ of FX for the VIIa/TF complex is between 0.061 and 0.099 μM based on the data shown in FIG. 7, consistent with published values (0.1 μM, Baugh, R. J. et al. (2000) *J. Biol. Chem.* 275(37):28826-28833). The concentration of FX in human plasma is 140 nM (1.4 to 2-fold $K_m$). An antibody such as scFv(TF)3e10, which does not compete with FX as shown in FIG. 7, will inhibit the activation of FX independent of the plasma concentration of FX.

EXAMPLE 6

In Vivo Rat Thromboembolism Model

Figure 8:
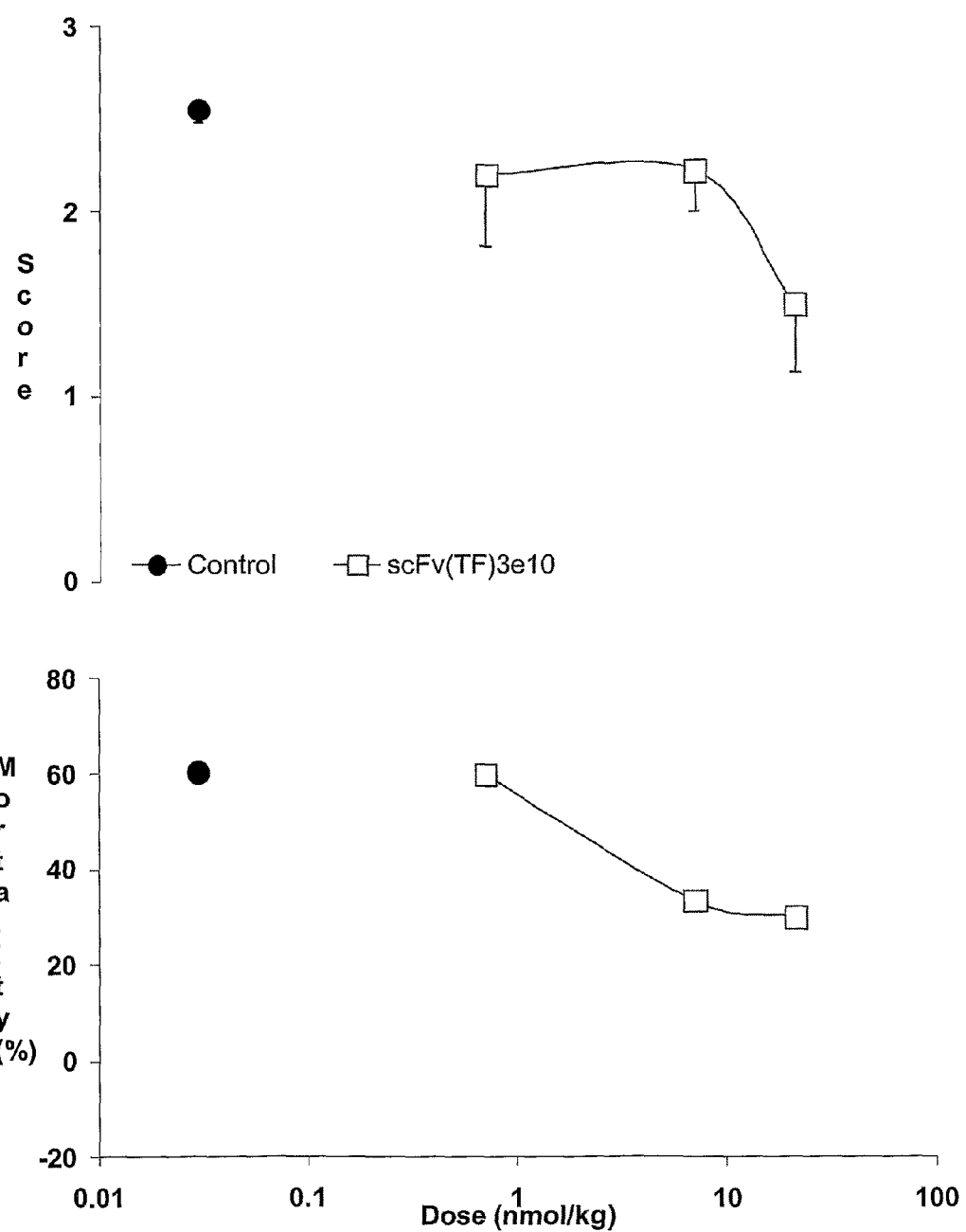
FIG. 8. scFv(TF)3e10 is efficacious in an in vivo model of disseminated intravascular coagulation ("DIC"). The TF-antibody scFV(TF)3e10 expressed in CHO cells was evaluated in the rat thromboembolism model described in Example 6 for (A) percent mortality and (B) morbidity-mortality score. (A) In the vehicle-treated group, the dose of TF used resulted in 60% lethality ($LD_{60}$). scFv(TF)3e10 at 0.7 nmol/kg had no impact on death, but at 7.0 nmol/kg reduced lethality to <40%. (B) In the vehicle-treated group, the in vivo dose of TF resulted in an average morbidity-mortality score of 2.6. scFv(TF)3e10 at 0.7 nmol/kg had no impact on death and little or no effect on respiratory distress, but at 14 nmol/kg, the average morbidity-mortality score was reduced to ~1.5.

The TF-binding single chain antibody scFv(TF)3e10 is specific for primate TF. A thromboembolism model triggered by human TF (thromboplastin reagent containing human recombinant TF, Ortho) was developed in conscious male Sprague-Dawley rats (350-400 g, n>7/group). In this model of disseminated intravascular coagulation (DIC), TF, via thromboplastin injection, induces pulmonary fibrin deposition, respiratory failure, and death. Doses of mammalian cell expressed scFv(TF)3e10 or vehicle were injected into the tail vein followed, 15 min later, by a bolus injection of thromboplastin (0.5 ml/kg). In the vehicle treated group, this dose of TF resulted in 60% lethality ($LD_{60}$), usually within 5 min after thromboplastin injection. The rats were scored according to the following morbidity-mortality scoring system: 0=unaffected; 1=mild respiratory distress (recover within 30 min); 2=severe respiratory distress (moribund, recovery required more than 60 min); and 3=death. The average score was used for comparing the efficacy of the different treatment groups. The results using this in vivo assay are depicted in FIG. 8. The antibody of the invention was able to reduce mortality and reduce respiratory distress in this assay.

The preceding examples can be repeated with similar success by substituting the generically or specifically described reactants and/or operating conditions of this invention for those used in the preceding examples.

While the invention has been illustrated with respect to the production of certain antibody constructs, it is apparent that variations and modifications of the invention can be made without departing from the spirit or scope of the invention.

The invention claimed is:

1. An isolated polynucleotide which encodes an anticoagulant antibody that binds with greater affinity to the factor VIIa/tissue factor (FVIIa/TF) complex than to tissue factor (TF) alone, wherein the antibody does not compete for binding to TF with FVII and FX and wherein the antibody comprises the amino acid sequence of SEQ ID NO:1 or SEQ ID NO:3.

2. The isolated polynucleotide of claim 1 which comprises the nucleotide sequence SEQ ID NO:2 or SEQ ID NO:4.

3. The isolated polynucleotide of claim 1 which is in a gene therapy vector.

4. The isolated polynucleotide of claim 1 which is a cDNA.

5. The isolated polynucleotide of claim 1 which is a synthetic DNA.

* * * * *

SEQUENCE LISTING

```
<160> NUMBER OF SEQ ID NOS: 4

<210> SEQ ID NO 1
<211> LENGTH: 282
<212> TYPE: PRT
<213> ORGANISM: artificial sequence
<220> FEATURE:
<223> OTHER INFORMATION: Amino acid sequence of scFv(TF) 3e10
      antibody

<400> SEQUENCE: 1

Met Leu Gly Val Leu Val Leu Gly Ala Leu Ala Leu Ala Gly Leu Val
1               5                   10                  15

Phe Pro Glu Met Ala Gln Val Asn Leu Arg Glu Ser Gly Gly Thr Leu
                20                  25                  30

Val Gln Pro Gly Gly Ser Leu Arg Leu Ser Cys Ala Ala Ser Gly Phe
            35                  40                  45

Ser Phe Thr Asp Ala Trp Met Ser Trp Val Arg Gln Ala Pro Gly Lys
        50                  55                  60

Glu Leu Glu Trp Val Ser Ser Ile Ser Gly Ser Gly Gly Ser Thr Tyr
65                  70                  75                  80

Tyr Ala Gly Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Val Leu Ser Leu Thr Asp Tyr Tyr Trp
        115                 120                 125

Tyr Gly Met Asp Val Trp Gly Gln Gly Thr Leu Val Thr Val Ser Ala
    130                 135                 140

Gly Gly Gly Gly Ser Gly Ala Pro Asn Phe Met Leu Thr Gln Pro His
145                 150                 155                 160

Ser Val Ser Ala Ser Pro Gly Lys Thr Val Thr Ile Ser Cys Thr Arg
                165                 170                 175
```

```
Ser Ser Gly Ser Val Ala Ser Tyr Tyr Val Gln Trp Tyr Gln Gln Arg
            180                 185                 190

Pro Gly Ser Ser Pro Thr Thr Val Ile Tyr Glu Asp Asn His Arg Pro
            195                 200                 205

Ser Gly Val Pro Asp Arg Phe Ser Gly Ser Ile Asp Thr Ser Ser Asn
            210                 215                 220

Ser Ala Ser Leu Thr Ile Ser Gly Leu Lys Thr Glu Asp Glu Ala Asp
225                 230                 235                 240

Tyr Tyr Cys Gln Ser Tyr Asp Ser Asn Asn Leu Val Val Phe Gly Gly
                245                 250                 255

Gly Thr Lys Leu Thr Val Leu Gly Ala Ala Ala Gly Ala Pro Val Pro
            260                 265                 270

Tyr Pro Asp Pro Leu Glu Pro Arg Ala Ala
            275                 280

<210> SEQ ID NO 2
<211> LENGTH: 849
<212> TYPE: DNA
<213> ORGANISM: artificial sequence
<220> FEATURE:
<223> OTHER INFORMATION: DNA sequence encoding scFv(TF) 3e10 antibody

<400> SEQUENCE: 2
atgcttgggg tcctggtcct tggcgcgctg gccctggcag gcctggtctt ccccgagatg      60
gcccaggtca acttaaggga gtctggggga accttggtcc agcctggggg gtccctgaga     120
ctctcctgtg cagcctctgg attcagtttc actgacgcct ggatgagctg ggtccgccag     180
gctccaggga aggagctgga gtgggtctca gtattagtgg tagtggtgg aagcacatac     240 tacgcaggct ccgtgaaggg ccggttcacc atctccagag acaattccaa gaacacgctg     300
tatctgcaaa tgaacagcct gagagccgag gacacggccg tatattactg tgcgagagta     360
ttatcgctga ccgattacta ctggtacggc atggacgtct ggggccaagg caccctggtc     420
accgtctcgg ccggtggcgg cggatctggc gcgccaaatt ttatgctgac tcagccccac     480
tctgtgtcgg cgtctccggg gaagacggta accatctcct gcacccgcag cagtggcagc     540
gttgccagct actatgtgca gtggtaccag cagcgcccgg gcagttcccc caccactgtg     600
atctatgagg ataaccacag accctctggg gtccctgatc ggttctctgg ctccatcgac     660
acctcctcca actctgcctc cctcaccatc tctggactga agactgagga cgaggctgac     720
tactactgtc agtcttatga tagcaacaac cttgtggttt tcggcggagg gaccaagctg     780
accgtcctag gtgcggccgc aggagctccg gtgccggatc cggatccgct ggaaccgcgt     840
gccgcatga                                                             849

<210> SEQ ID NO 3
<211> LENGTH: 261
<212> TYPE: PRT
<213> ORGANISM: artificial sequence
<220> FEATURE:
<223> OTHER INFORMATION: Amino acid sequence of scFv(TF) 3e10delta
      antibody

<400> SEQUENCE: 3

Met Leu Gly Val Leu Val Leu Gly Ala Leu Ala Leu Ala Gly Leu Val
1               5                   10                  15

Phe Pro Glu Met Ala Gln Val Asn Leu Arg Glu Ser Gly Gly Thr Leu
            20                  25                  30

Val Gln Pro Gly Gly Ser Leu Arg Leu Ser Cys Ala Ala Ser Gly Phe
        35                  40                  45
```

```
Ser Phe Thr Asp Ala Trp Met Ser Trp Val Arg Gln Ala Pro Gly Lys
 50                  55                  60

Glu Leu Glu Trp Val Ser Ser Ile Ser Gly Ser Gly Gly Ser Thr Tyr
 65                  70                  75                  80

Tyr Ala Gly Ser Val Lys Gly Arg Phe Thr Ile Ser Arg Asp Asn Ser
                 85                  90                  95

Lys Asn Thr Leu Tyr Leu Gln Met Asn Ser Leu Arg Ala Glu Asp Thr
            100                 105                 110

Ala Val Tyr Tyr Cys Ala Arg Val Leu Ser Leu Thr Asp Tyr Tyr Trp
            115                 120                 125

Tyr Gly Met Asp Val Trp Gly Gln Gly Thr Leu Val Thr Val Ser Ala
130                 135                 140

Gly Gly Gly Gly Ser Asn Phe Met Leu Thr Gln Pro His Ser Val Ser
145                 150                 155                 160

Ala Ser Pro Gly Lys Thr Val Thr Ile Ser Cys Thr Arg Ser Ser Gly
                165                 170                 175

Ser Val Ala Ser Tyr Tyr Val Gln Trp Tyr Gln Gln Arg Pro Gly Ser
            180                 185                 190

Ser Pro Thr Thr Val Ile Tyr Glu Asp Asn His Arg Pro Ser Gly Val
            195                 200                 205

Pro Asp Arg Phe Ser Gly Ser Ile Asp Thr Ser Ser Asn Ser Ala Ser
210                 215                 220

Leu Thr Ile Ser Gly Leu Lys Thr Glu Asp Glu Ala Asp Tyr Tyr Cys
225                 230                 235                 240

Gln Ser Tyr Asp Ser Asn Asn Leu Val Val Phe Gly Gly Gly Thr Lys
                245                 250                 255

Leu Thr Val Leu Gly
            260

<210> SEQ ID NO 4
<211> LENGTH: 783
<212> TYPE: DNA
<213> ORGANISM: artificial sequence
<220> FEATURE:
<223> OTHER INFORMATION: DNA sequence encoding scFv(TF) 3e10delta
      antibody

<400> SEQUENCE: 4
atgcttgggg tcctggtcct tggcgcgctg gccctggcag gcctggtctt ccccgagatg      60
gcccaggtca acttaaggga gtctggggga accttggtcc agcctggggg gtccctgaga     120
ctctcctgtg cagcctctgg attcagtttc actgacgcct ggatgagctg ggtccgccag     180
gctccaggga aggagctgga gtgggtctca gtattagtg gtagtggtgg aagcacatac      240
tacgcaggct ccgtgaaggg ccggttcacc atctccagag acaattccaa gaacacgctg     300
tatctgcaaa tgaacagcct gagagccgag gacacggccg tatattactg tgcgagagta     360
ttatcgctga ccgattacta ctggtacggc atggacgtct ggggccaagg caccctggtc     420
accgtctcgg ccgtggcggc ggatctaat tttatgctga ctcagcccca ctctgtgtcg     480
gcgtctccgg ggaagacggt aaccatctcc tgcacccgca gcagtggcag cgttgccagc     540
tactatgtgc agtggtacca gcagcgcccg ggcagttccc ccaccactgt gatctatgag     600
```

-continued

| | | | | |
|---|---|---|---|---|
| gataaccaca | gaccctctgg | ggtccctgat | cggttctctg | gctccatcga cacctcctcc 660 |
| aactctgcct | ccctcaccat | ctctggactg | aagactgagg | acgaggctga ctactactgt 720 |
| cagtcttatg | atagcaacaa | ccttgtggtt | ttcggcggag | ggaccaagct gaccgtccta 780 |
| ggt | | | | 783 |